United States Patent [19]

Nakamura et al.

[11] Patent Number: 5,593,616
[45] Date of Patent: Jan. 14, 1997

[54] OPTICALLY INACTIVE, MESOMORPHIC COMPOUND, LIQUID CRYSTAL COMPOSITION CONTAINING THE COMPOUND, LIQUID CRYSTAL DEVICE USING THE COMPOSITION, LIQUID CRYSTAL APPARATUS AND DISPLAY METHOD

[75] Inventors: Shinichi Nakamura, Isehara; Takao Takiguchi, Tokyo; Takashi Iwaki, Machida; Takeshi Togano, Yokohama; Yoko Kosaka, Atsugi, all of Japan

[73] Assignee: Canon Kabushiki Kaisha, Tokyo, Japan

[21] Appl. No.: 306,450

[22] Filed: Sep. 19, 1994

[30] Foreign Application Priority Data

Sep. 17, 1993 [JP] Japan ..................... 5-231678

[51] Int. Cl.⁶ .................. C09K 19/34; G02F 1/13
[52] U.S. Cl. .................. 252/299.61; 349/171; 349/184
[58] Field of Search ............ 252/299.61, 299.01; 359/100, 103, 104

[56] References Cited

U.S. PATENT DOCUMENTS

| | | | |
|---|---|---|---|
| 4,367,924 | 1/1983 | Clark et al. ............... | 350/334 |
| 4,684,476 | 8/1987 | Kitano et al. ............. | 252/299.61 |
| 4,871,469 | 10/1989 | Reiffenrath et al. ....... | 252/299.61 |
| 5,173,211 | 12/1992 | Yamashita et al. ....... | 252/299.61 |
| 5,190,688 | 3/1993 | Sage et al. ............... | 252/299.01 |
| 5,240,637 | 8/1993 | Shinjo et al. ............. | 252/299.61 |
| 5,328,640 | 7/1994 | Shinjo et al. ............. | 252/299.61 |

FOREIGN PATENT DOCUMENTS

| | | |
|---|---|---|
| 0193191 | 9/1986 | European Pat. Off. . |
| 0451854 | 10/1991 | European Pat. Off. . |
| 56-107216 | 8/1981 | Japan . |
| 63-027451 | 2/1988 | Japan . |
| 1233262 | 9/1989 | Japan . |
| 1230548 | 9/1989 | Japan . |
| 2069443 | 3/1990 | Japan . |
| 2142753 | 5/1990 | Japan . |
| 3093748 | 4/1991 | Japan . |
| 26679 | 1/1992 | Japan . |
| 4026679 | 1/1992 | Japan . |
| 00897 | 1/1991 | WIPO . |

OTHER PUBLICATIONS

M. Schadt and W. Helfrich, Voltage-Dependent Optical Activity of a Twisted Nematic Liquid Crystal, Feb. 1971, pp. 127–128, APL, vol. 18, No. 4.

*Primary Examiner*—Shean C. Wu
*Attorney, Agent, or Firm*—Fitzpatrick, Cella, Harper & Scinto

[57] ABSTRACT

An optically inactive mesomorphic compound represented by the following formula (I):

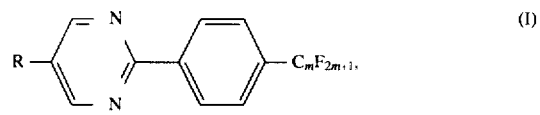

wherein R denotes a linear or branched alkyl group having 1–18 carbon atoms or a linear or branched alkoxy group having 1–18 carbon atoms; and m is an integer of 2–18, is suitable as a component for a liquid crystal composition providing improved response characteristics and a high contrast. A liquid crystal device is constituted by disposing the liquid crystal composition between a pair of substrates. The liquid crystal device may preferably be used as a display panel constituting a liquid crystal apparatus providing good display characteristics.

19 Claims, 8 Drawing Sheets

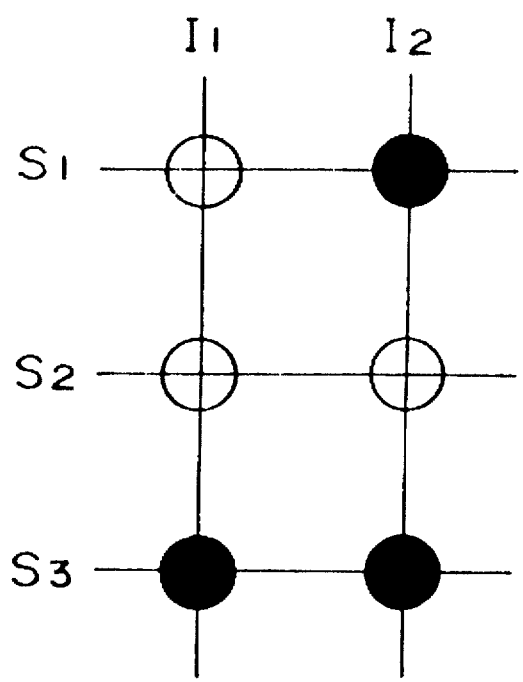
F I G. 6

OPTICALLY INACTIVE, MESOMORPHIC COMPOUND, LIQUID CRYSTAL COMPOSITION CONTAINING THE COMPOUND, LIQUID CRYSTAL DEVICE USING THE COMPOSITION, LIQUID CRYSTAL APPARATUS AND DISPLAY METHOD

FIELD OF THE INVENTION AND RELATED ART

The present invention relates to a mesomorphic compound, a liquid crystal composition, a liquid crystal device, a display apparatus and a display method, and more particularly to an optically inactive mesomorphic compound, a liquid crystal composition containing the compound with improved responsiveness to an electric field, a liquid crystal device using the composition for use in a display device, a liquid crystal-optical shutter, etc., a liquid crystal apparatus using the device particularly as a display device, and a display method of using the composition.

Hitherto, liquid crystal devices have been used as an electro-optical device in various fields. Most liquid crystal devices which have been put into practice use TN (twisted nematic) type liquid crystals, as shown in "Voltage-Dependent Optical Activity of a Twisted Nematic Liquid Crystal" by M. Schadt and W. Helfrich "Applied Physics Letters" Vol. 18, No. 4 (Feb. 15, 1971) pp. 127–128.

These devices are based on the dielectric alignment effect of a liquid crystal and utilize an effect that the average molecular axis direction is directed to a specific direction in response to an applied electric field because of the dielectric anisotropy of liquid crystal molecules. It is said that the limit of response speed is on the order of μsec, which is too slow for many uses. On the other hand, a simple matrix system of driving is most promising for application to a large-area flat display in view of cost, productivity, etc., in combination. In the simple matrix system, an electrode arrangement wherein scanning electrodes and signal electrodes are arranged in a matrix, and for driving, a multiplex driving scheme is adopted wherein an address signal is sequentially, periodically and selectively applied to the scanning electrodes and prescribed data signals are selectively applied in parallel to the signal electrodes in synchronism with the address signal.

When the above-mentioned TN-type liquid crystal is used in a device of such a driving system, a certain electric field is applied to regions where a scanning electrode is selected and signal electrodes are not selected (or regions where a scanning electrode is not selected and a signal electrode is selected), which regions are called "half-selected points". If the difference between a voltage applied to the selected points and a voltage applied to the half-selected points is sufficiently large, and a voltage threshold level required for allowing liquid crystal molecules to be aligned or oriented perpendicular to an electric field is set to a value therebetween, display devices normally operate. However, in fact, as the number (N) of scanning lines increases, a time (duty ratio) during which an effective electric field is applied to one selected point when a whole image area (corresponding to one frame) is scanned decreases with a ratio of 1/N. Accordingly, the larger the number of scanning lines are, the smaller is the voltage difference of an effective value applied to a selected point and non-selected points when scanning is repeatedly effected. This leads to unavoidable drawbacks of lowering of image contrast or occurrence of interference or crosstalk. These phenomena are regarded as essentially unavoidable problems appearing when a liquid crystal having no bistability (i.e. liquid crystal molecules are horizontally oriented with respect to the electrode surface as stable state and is vertically oriented with respect to the electrode surface only when an electric field is effectively applied) is driven (i.e. repeatedly scanned) by making use of a time storage effect. To overcome these drawbacks, the voltage averaging method, the two-frequency driving method, the multiple matrix method, etc. have been already proposed. However, any method is not sufficient to overcome the above-mentioned drawbacks. As a result, the development of large image area or high packaging density in respect to display elements is delayed because it is difficult to sufficiently increase the number of scanning lines.

To overcome drawbacks with such prior art liquid crystal devices, the use of liquid crystal devices having bistability has been proposed by Clark and Lagerwall (e.g. Japanese Laid-Open Patent Appln. No. 56-107216; U.S. Pat. No. 4,367,924, etc.). In this instance, as the liquid crystals having bistability, ferroelectric liquid crystals having chiral smectic C-phase (SmC*) or H-phase (SmH*) are generally used. These liquid crystals have bistable states of first and second stable states with respect to an electric field applied thereto. Accordingly, as different from optical modulation devices in which the above-mentioned TN-type liquid crystals are used, the bistable liquid crystal molecules are oriented to first and second optically stable states with respect to one and the other electric field vectors, respectively. Further, this type of liquid crystal has a property (bistability) of assuming either one of the two stable states in response to an applied electric and retaining the resultant state in the absence of an electric field.

In addition to the above-described characteristic of showing bistability, such a ferroelectric liquid crystal (hereinafter sometimes abbreviated as "FLC") has an excellent property, i.e., a high-speed responsiveness. This is because the spontaneous polarization of the ferroelectric liquid crystal and an applied electric field directly interact with each other to induce transition of orientation states. The resultant response speed is faster than the response speed due to the interaction between dielectric anisotropy and an electric field by 3 to 4 digits.

Thus, a ferroelectric liquid crystal potentially has very excellent characteristics, and by making use of these properties, it is possible to provide essential improvements to many of the above-mentioned problems with the conventional TN-type devices. Particularly, the application to a high-speed optical shutter and a display of a high density and a large picture is expected. For this reason, there has been made extensive research with respect to liquid crystal materials showing ferroelectricity. However, previous ferroelectric liquid crystal materials do not sufficiently satisfy characteristics required for a liquid crystal device including low-temperature operation characteristic, high-speed responsiveness, high contrast, etc.

More specifically, among a response time $\tau$, the magnitude of spontaneous polarization Ps and viscosity $\eta$, the following relationship (II) exists: $\tau = \eta/(Ps \cdot E)$ ... (II), where E is an applied voltage. Accordingly, a high response speed can be obtained by (a) increasing the spontaneous polarization Ps, (b) lowering the viscosity $\eta$, or (c) increasing the applied voltage E. However, the driving voltage has a certain upper limit in view of driving with IC, etc., and should desirably be as low as possible. Accordingly, it is actually necessary to lower the viscosity or increase the spontaneous polarization.

A ferroelectric chiral smectic liquid crystal having a large spontaneous polarization generally provides a large internal electric field in a cell given by the spontaneous polarization and is liable to pose many constraints on the device construction giving bistability. Further, an excessively large spontaneous polarization is liable to accompany an increase in viscosity, so that remarkable increase in response speed may not be attained as a result.

Moreover, if it is assumed that the operation temperature of an actual display device is 5°–40° C., the response speed changes by a factor of about 20, so that it actually exceeds the range controllable by driving voltage and frequency.

In general, in a liquid crystal device utilizing birefringence of a liquid crystal, the transmittance under right angle cross nicols is given by the following equation:

$$I/I_O = \sin^2 4\theta \cdot \sin^2(\Delta n d/\lambda)\pi,$$

wherein $I_O$: incident light intensity,

I: transmitted light intensity,

θ: tilt angle,

Δn: refractive index anisotropy, d: thickness of the liquid crystal layer,

λ: wavelength of the incident light.

Tilt angle θ in a ferroelectric liquid crystal with non-helical structure is recognized as a half of an angle between the average molecular axis directions of liquid crystal molecules in a twisted alignment in a first orientation state and a second orientation state. According to the above equation, it is shown that a tilt angle θ of 22.5 degrees provides a maximum transmittance and the tilt angle θ in a non-helical structure for realizing bistability should desirably be as close as possible to 22.5 degrees in order to provide a high transmittance and a high contrast.

However, when a birefringence of a liquid crystal is utilized in a liquid crystal device using a ferroelectric liquid crystal in a non-helical structure exhibiting bistability reported by Clark and Lagerwall, the following problems are encountered, thus leading to a decrease in contrast.

First, a tile angle θ in a ferroelectric liquid crystal with a non-helical structure obtained by alignment with a polyimide film treated by rubbing of the prior art has become smaller as compared with a tilt angle Ⓗ (the angle Ⓗ is a half of the apex angle of the cone shown in FIG. 4 as described below) in the ferroelectric liquid crystal having a helical structure, thus resulting in a lower transmittance.

Secondly, even if the device provides a high contrast in a static state, i.e., under no electric field application, liquid crystal molecules fluctuate due to a slight electric field at a non-selection period of time in a matrix drive scheme in the case of applying a voltage to the liquid crystal molecules for providing a display image, thus resulting in the display image including a light (or pale) black display state, i.e., a decrease in a contrast.

Thus, as described hereinabove, commercialization of a ferroelectric liquid crystal device requires a liquid crystal composition assuming a chiral smectic phase which provides a high contrast, a high-speed responsiveness and a small temperature-dependence of response speed.

In order to afford uniform switching characteristics at display, a good view-angle characteristic, a good storage stability at a low temperature, a decrease in a load to a driving IC (integrated circuit), etc. to the above-mentioned ferroelectric liquid crystal device or a display apparatus including the ferroelectric liquid crystal device, the above-mentioned liquid crystal composition is required to optimize its properties such as spontaneous polarization, an chiral smectic C (SmC*) pitch, a cholesteric (Ch) pitch, a temperature range showing a mesomorphic phase, optical anisotropy, a tilt angle and dielectric anisotropy.

SUMMARY OF THE INVENTION

An object of the present invention is to provide a mesomorphic compound providing a high speed responsiveness, a high contrast and a decreased temperature-dependence of response speed; a liquid crystal composition, particularly a chiral smectic liquid crystal composition containing the mesomorphic compound for providing a practical ferroelectric liquid crystal device as described above; a liquid crystal device including the liquid crystal composition and affording good display performances; a liquid crystal apparatus including the device; and a display method using the composition.

According to the present invention, there is provided an optically inactive mesomorphic compound represented by the following formula (I):

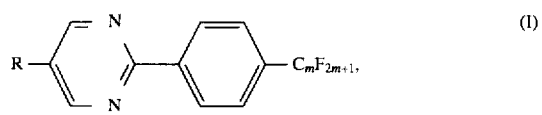

wherein R denotes a linear or branched alkyl group having 1–18 carbon atoms or a linear or branched alkoxy group having 1–18 carbon atoms: and m is an integer of 2–18.

According to the present invention, there is further provided a liquid crystal composition containing at least one species of the above-mentioned mesomorphic compound.

The present invention provides a liquid crystal device comprising a pair of substrates and the liquid crystal composition described above disposed between the substrates.

The present invention further provides a liquid crystal apparatus including the liquid crystal device, particularly including a display panel comprising the liquid crystal device.

The present invention still further provides a display method of using the liquid crystal composition described above and controlling the alignment direction of liquid crystal molecules to effect display.

Heretofore, there have been known (mesomorphic) compounds having a perfluoroalkyl group as disclosed in Japanese Laid-Open Patent Applications (JP-A) (Kokai) Nos. 63-27451, 2-142753, 1-230548, 1-233262 and 2-69443.

These compounds have a linkage between a terminal perfluoroalkyl group and an inner mesogen skeleton. The linkage is ether group or ester group respectively containing methylene group or ethylene group. Thus, these compounds are distinguished from the above-mentioned mesomorphic compound of the formula (I) containing a mesogen skeleton

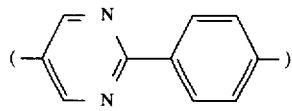

and a perfluoroalkyl group ($C_mF_{2m-1}$) directly connected to the mesogen skeleton (i.e.,

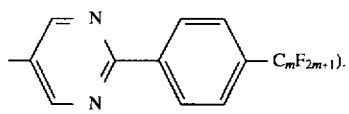

JP-A (Kokai) 3-93748, 4-26679 and U.S. Pat. No. 4,871,469 respectively disclose compounds capable of containing a mesogen skeleton and a perfluoroalkyl group directly connected to each other. However, the compounds disclosed in JP-A 3-93748 are limited to an optically active compound and JP-A 4-26679 and U.S. Pat. No. 4,871,469 fail to disclose specific compounds containing such a mesogen skeleton and perfluoroalkyl group directly connected to each other, thus being different from the optically inactive mesomorphic compound of the formula (I) according to the present invention. JP-A (Kohyo) 1-501945 discloses compounds containing a cyclohexane ring

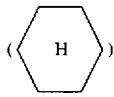

and a perfluoroalkyl group directly connected to the cyclohexane ring. On the other hand, the mesomorphic compound of the formula (I) has the mesogen skeleton

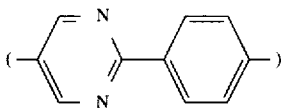

containing no cyclohexane ring, thus being different from the compounds of JP-A 1-501945.

We have found that an optically inactive mesomorphic compound represented by the formula (I) is suitable as a component of a liquid crystal composition, particularly a ferroelectric chiral smectic liquid crystal composition, and a liquid crystal device including the liquid crystal composition which provide good display characteristics based on improvements in various characteristics such as an alignment characteristic, switching characteristic, responsiveness, a temperature-dependence of response speed, a contrast, and a stability of a mesomorphic phase.

These and other objects, features and advantages of the present invention will become more apparent upon a consideration of the following description of the preferred embodiments of the present invention taken in conjunction with the accompanying drawings.

DESCRIPTION OF THE DRAWINGS

FIG. 6 is an illustration of a display pattern obtained by an actual drive using the time-serial waveforms shown in FIG. 5B;

DETAILED DESCRIPTION OF THE INVENTION

Figure 1:
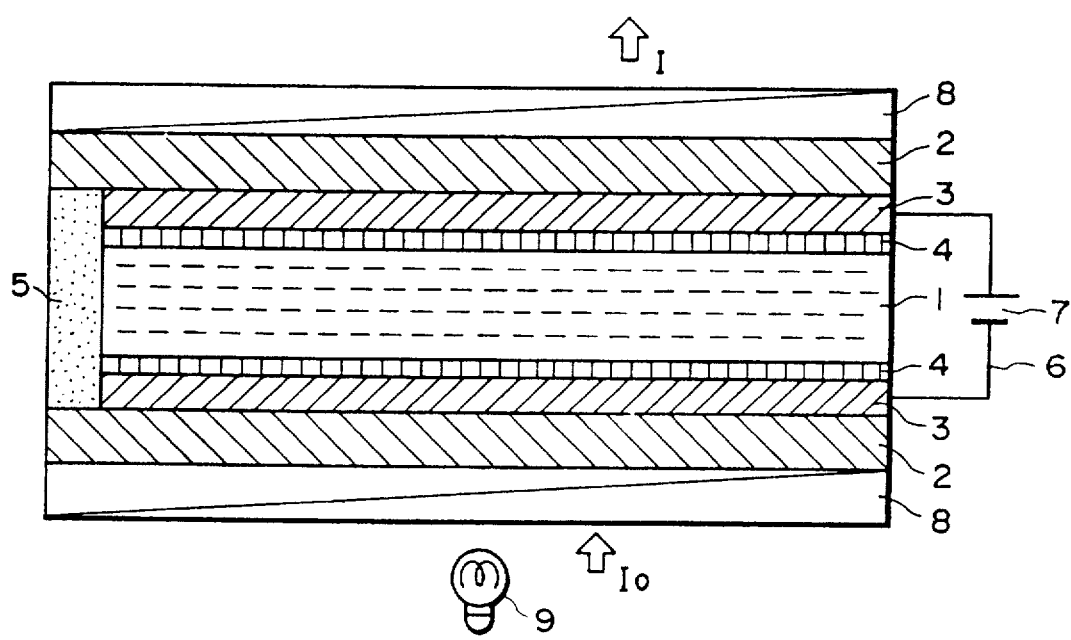
FIG. 1 is a schematic sectional view of a liquid crystal device using a liquid crystal composition assuming a chiral smectic phase.

The optically inactive mesomorphic compound of the formula (I) according to the present invention is characterized by containing a mesogen skeleton

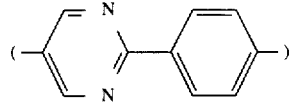

directly connected with a terminal perfluoroalkyl group ($C_mF_{2m+1}$) having at least two carbon atoms. Based on such a structural characteristic, the optically inactive compound of the formula (I) is effective for improving various characteristics of a resultant liquid crystal composition, such as a switching characteristic, responsiveness, a temperature-dependence of response speed, and a contrast.

In view of improvements in various properties including: a temperature range of a mesomorphic phase, miscibility or compatibility, viscosity, temperature-dependence of response speed, alignment characteristic and contrast, the mesomorphic compound of the formula (I) may preferably include those having a terminal perfluoroalkyl group ($—C_mF_{2m+1}$) in which m is 3–12 or those having a terminal group (—R) comprising a linear alkyl group having 3–14 carbon atoms or a linear alkoxy group having 3–14 carbon atoms.

In order to improve a temperature-dependence of response speed of a resultant liquid crystal composition (or device), the mesomorphic compound of the formula (I) may preferably have a terminal perfluoroalkyl group ($—C_mF_{2m+1}$) in which m is 6–18, particularly 9–18.

The mesomorphic compound of the formula (I) may generally be synthesized through, e.g., the following reaction scheme.

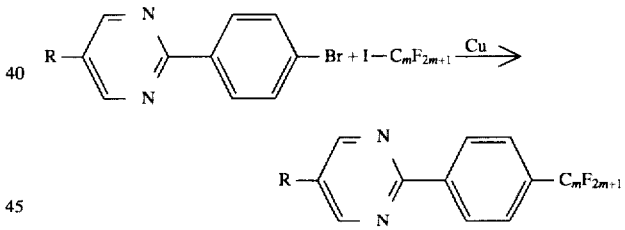

In the above reaction scheme, R and m each have the meaning defined above.

Herein, the term "mesomorphic compound" covers not only a compound assuming a mesomorphic (liquid crystal) phase but also a compound not assuming a mesomorphic phase per se as long as a liquid crystal composition containing such a compound assumes a mesomorphic phase.

Specific examples of the optically inactive mesomorphic compound of the formula (I) may include those represented by the following structural formulae (Example Compounds Nos. (1) to (50) including abbreviations for respective cyclic groups listed below.

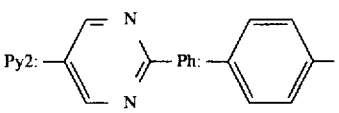

(1) $CH_3—Py2—Ph—C_{18}F_{37}$
(2) $C_{14}H_{29}—Py2—Ph—C_3F_7$ (3) $C_2H_5O$—Py2—Ph—$C_{17}F_{35}$
(4) $C_2H_5$—Py2—Ph—$C_{10}F_{21}$
(5) $C_{14}H_{29}$—Py2—Ph—$C_2F_5$
(6) $C_3H_7O$—Py2—Ph—$C_{11}F_{23}$
(7) $C_3H_7$—Py2—Ph—$C_{16}F_{33}$
(8) $C_{15}H_{31}O$—Py2—Ph—$C_8F_{17}$
(9) $C_4H_9$—Py2—Ph—$C_{12}F_{25}$
(10) $C_4H_9$—Py2—Ph—$C_9F_{19}$
(11) $C_2H_5CH(CH_3)CH_2O$—Py2—Ph—$C_6F_{13}$
(12) $CH_3CH(CH_3)CH_2CH_2O$—Py2—Ph—$C_8F_{17}$
(13) $C_2H_5CH(C_2H_5)CH_2CH_2O$—Py2—Ph—$C_9F_{19}$
(14) $C_4H_9$—Py2—Ph—$C_8F_{17}$
(15) $C_5H_{11}O$—Py2—Ph—$C_6F_{13}$
(16) $C_5H_{11}$—Py2—Ph—$C_5F_{11}$
(17) $C_5H_{11}$—Py2—Ph—$C_{10}F_{21}$
(18) $C_{16}H_{33}$—Py2—Ph—$C_4F_9$
(19) $C_6H_{13}O$—Py2—Ph—$C_6F_{13}$

(20) $C_6H_{13}$—Py2—Ph—$C_8F_{17}$
(21) $C_6H_{13}$—Py2—Ph—$C_{10}F_{21}$
(22) $C_{17}H_{35}$—Py2—Ph—$C_5F_{11}$
(23) $C_7H_{15}O$—Py2—Ph—$C_6F_{13}$
(24) $CH_3CH(CH_3)(CH_2)_3$—Py2—Ph—$C_7F_{15}$
(25) $C_2H_5CH(CH_3)(CH_2)_5$—Py2—Ph—$C_{10}F_{21}$
(26) $C_4H_9CH(CH_3)(CH_2)_2$—Py2—Ph—$C_{12}F_{25}$
(27) $C_7H_{15}$—Py2—Ph—$C_7F_{15}$
(28) $C_7H_{15}$—Py2—Ph—$C_8F_{17}$
(29) $C_{18}H_{37}$—Py2—Ph—$C_4F_9$
(30) $C_8H_{17}O$—Py2—Ph—$C_9F_{19}$
(31) $C_8H_{17}$—Py2—Ph—$C_{10}F_{21}$
(32) $C_8H_{17}$—Py2—Ph—$C_{11}F_{23}$
(33) $C_8H_{17}O$—Py2—Ph—$C_{12}F_{25}$
(34) $C_9H_{19}$—Py2—Ph—$C_6F_{13}$
(35) $C_9H_{19}$—Py2—Ph—$C_9F_{19}$
(36) $C_9H_{19}O$—Py2—Ph—$C_{10}F_{21}$
(37) $C_{12}H_{25}$—Py2—Ph—$C_8F_{17}$
(38) $C_{12}H_{25}O$—Py2—Ph—$C_7F_{15}$
(39) $C_{13}H_{27}$—Py2—Ph—$C_5F_{11}$
(40) $C_{10}H_{21}$—Py2—Ph—$C_6F_{13}$
(41) $C_{10}H_{21}$—Py2—Ph—$C_7F_{15}$
(42) $C_{10}H_{21}O$—Py2—Ph—$C_8F_{17}$
(43) $C_{11}H_{23}$—Py2—Ph—$C_5F_{11}$
(44) $C_{11}H_{23}$—Py2—Ph—$C_6F_{13}$
(45) $C_{11}H_{23}O$—Py2—Ph—$C_7F_{15}$
(46) $C_{12}H_{25}$—Py2—Ph'$C_9F_{19}$
(47) $C_9H_{19}$—Py2—Ph—$C_8F_{17}$
(48) $C_8H_{17}$—Py2—Ph—$C_8F_{17}$
(49) $C_9H_{19}$—Py2—Ph—$C_4F_9$
(50) $C_{10}H_{21}$—Py2—Ph—$C_5F_{11}$

The liquid crystal composition according to the present invention may be obtained by mixing at least one species, preferably at least two species, of the mesomorphic compound represented by the formula (I) and at least one species, preferably 1–50 species, more preferably 1–30 species, particularly 3–30 species, of another mesomorphic compound, in appropriate proportions determined by taking account of usage or uses of a liquid crystal device using the composition, characteristics required therefor, etc.

In order to improve a temperature-dependence of response speed and/or a low-temperature operation characteristic, the liquid crystal composition of the present invention may preferably contain at least one species, more preferably at least two species, of the mesomorphic compound of the formula (I) having —$C_mF_{2m+1}$ in which m is 3–18, preferably 6–18, more preferably 9–18.

The liquid crystal composition according to the present invention may preferably be formulated as a liquid crystal composition capable of showing ferroelectricity, particularly a liquid crystal composition showing a chiral smectic phase.

Specific examples of another mesomorphic compound described above may include those denoted by the following formulae (III) to (XII).

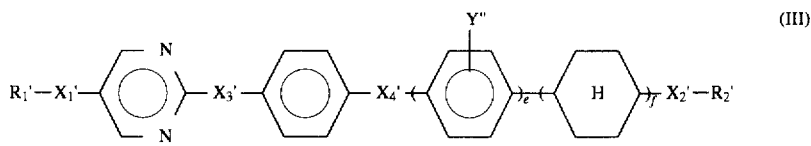

(III)

wherein e denotes 0 or 1 and f denotes 0 or 1 with proviso that e+f=0 or 1; Y" denotes H, halogen, $CH_3$ or $CF_3$; and $X_1'$ and $X_2'$ respectively denote a single bond,

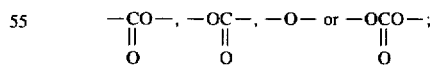

$X_3'$ and $X_4'$ respectively denote a single bond,

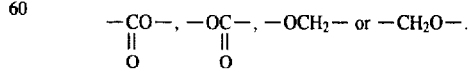

In the formula (III), preferred compounds thereof may include those represented by the following formulas (IIIa) to (IIIe):

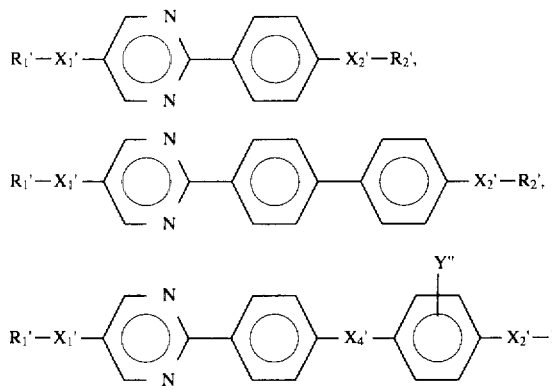
(IIIa)
(IIIb)
(IIIc)

and

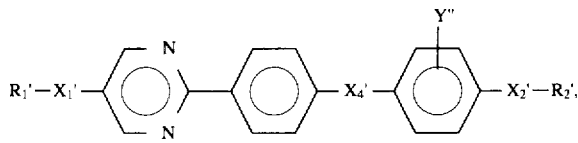
(IIId)

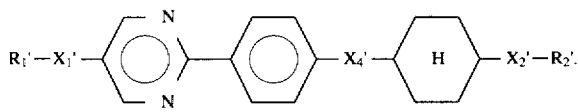
(IV)

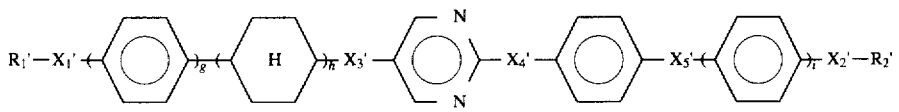

wherein g and h respectively denote 0 or 1 with proviso that g+h=0 or 1; i denotes 0 or 1; $X_1'$ and $X_2'$ respectively denote a single bond,

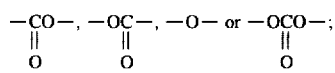

and $X_3'$, $X_4'$, and $X_5'$ respectively denote a single bond,

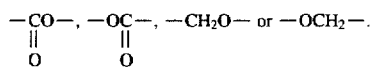

In the formula (IV), preferred compounds thereof may include those represented by the following formulas (IVa) to (IVc):

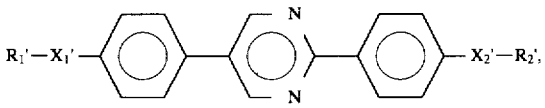
(IVa)

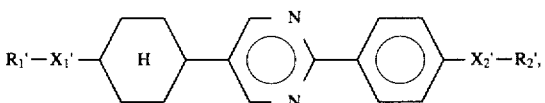
(IVb)

and

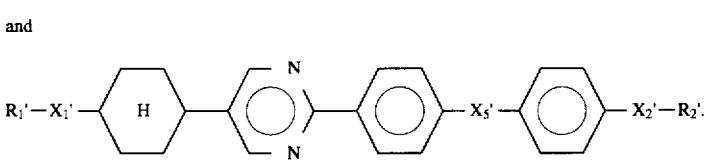
(IVc)

wherein j denotes 0 or 1; $Y_1''$, $Y_2''$ and $Y_3''$ respectively denote H, halogen, $CH_3$ or $CF_3$; $X_1'$ and $X_2'$ respectively denote a single bond,

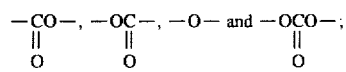

and $X_3'$ and $X_4'$ respectively denote a single bond,

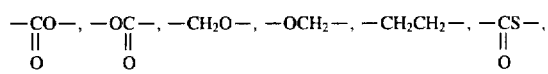
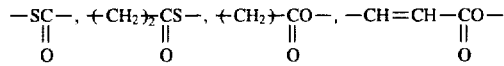

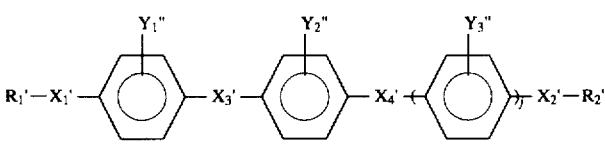
(V)

or

—O—.

In the formula (V), preferred compounds thereof may include those represented by the following formulas (Va) and (Vb):

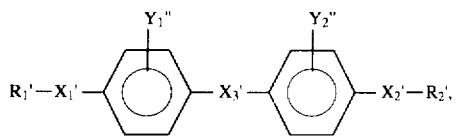
(Va)

and

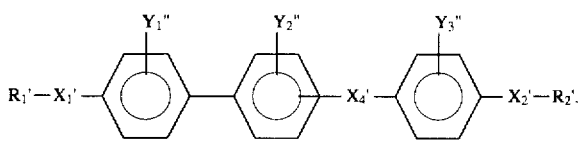
(Vb)

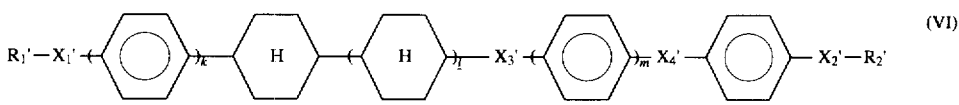
(VI)

wherein k, l and m respectively denote 0 or 1 with proviso that k+l+m=0, 1 or 2; $X_1'$ and $X_2'$ respectively denote a single bond,

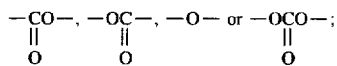

and $X_3'$ and $X_4'$ respectively denote a single bond,

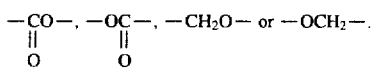

In the formula (VI), preferred compounds thereof may include those represented by the following formulas (VIa) to (VIf):

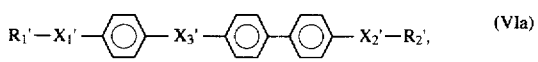 (VIa)

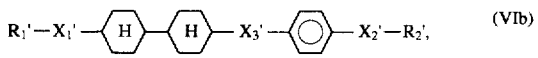 (VIb)

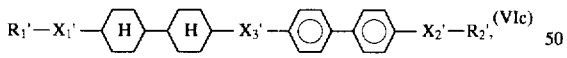 (VIc)

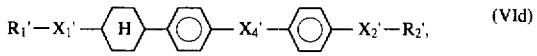 (VId)

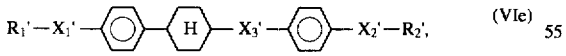 (VIe)

and

 (VIf)

Herein, $R_1'$ and $R_2'$ respectively denote a linear or branched alkyl group having 1–18 carbon atoms capable of including one or non-neighboring two or more methylene groups which can be replaced with —CH halogen— and capable of further including one or two or more non-neighboring methylene groups other than those directly connected to $X_1'$ or $X_2'$ which can be replaced with at least one species of

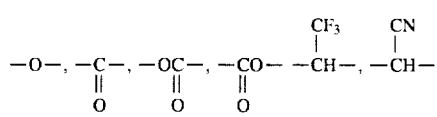

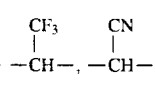

-continued and

with proviso that $R_1'$ and $R_2'$ respectively do not connect to a ring structure by a single bond when $R_1'$ and $R_2'$ respectively denote a halogenated alkyl group containing one methylene group replaced with —CH halogen—or —CH(CF$_3$)—.

Further, preferred examples of $R_1'$ and $R_2'$ may respectively include those represented by the following groups (i) to (ix):

i) a linear alkyl group having 1–15 carbon atoms;

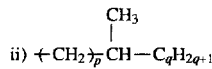

wherein p denotes an integer of 0–5 and q denotes an integer of 2–11 (optically active or inactive);

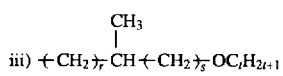

wherein r denotes an integer of 0–6, s denotes 0 or 1, and t denotes an integer of 1–14 (optically active or inactive);

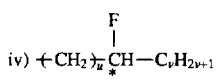

wherein u denotes 0 or 1 and v denotes an integer of 1–16;

v) 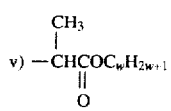

wherein w denotes an integer of 1–15 (optically active or inactive);

vi) 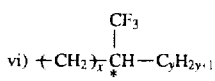

wherein x denotes an integer of 0–2 and y denotes an integer of 1–15 ;

vii) 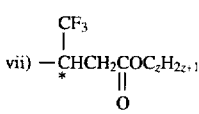

wherein z denotes an integer of 1–15 ;

viii) 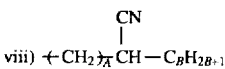

wherein A denotes an integer of 0–2 and B denotes an integer of 1–15 (optically active or inactive); and ix) 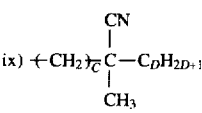

wherein C denotes an integer of 0–2 and D denotes an integer of 1–15 (optically active or inactive).

In the above-mentioned formulas (IIIa) to (IIId), more preferred compounds thereof may include those represented by the formulas (IIIaa) to (IIIdc):

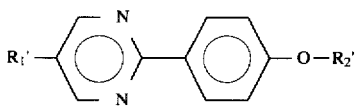 (IIIaa)

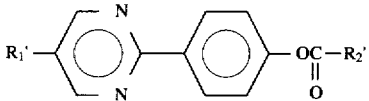 (IIIab)

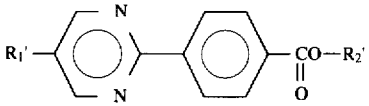 (IIIac)

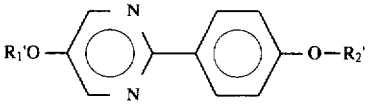 (IIIad)

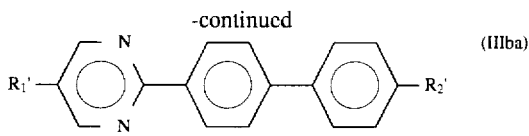 (IIIba)

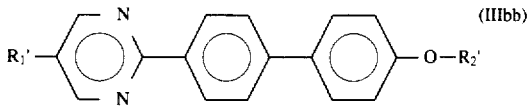 (IIIbb)

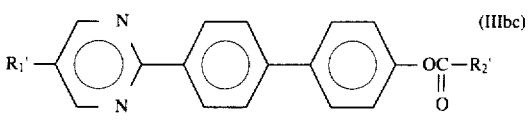 (IIIbc)

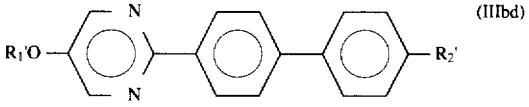 (IIIbd)

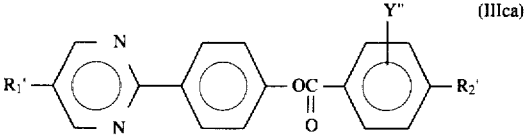 (IIIca)

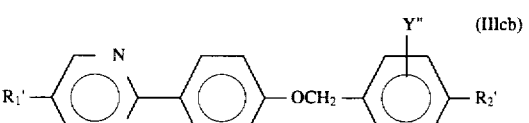 (IIIcb)

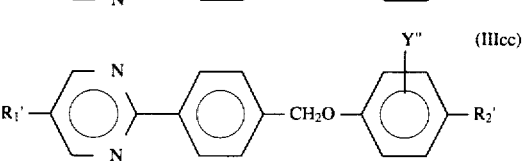 (IIIcc)

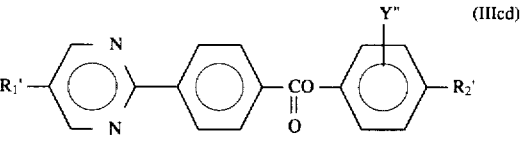 (IIIcd)

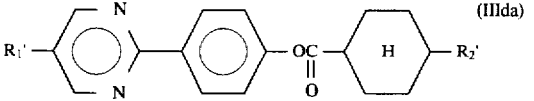 (IIIda)

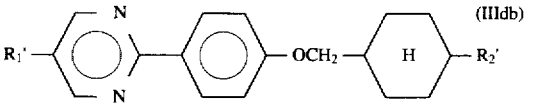 (IIIdb)

and

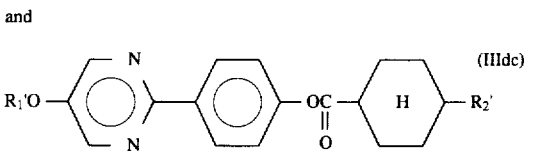 (IIIdc)

In the above-mentioned formulas (IVa) to (IVc), more preferred compounds thereof may include those represented by the formulas (IVaa) to (IVcb):

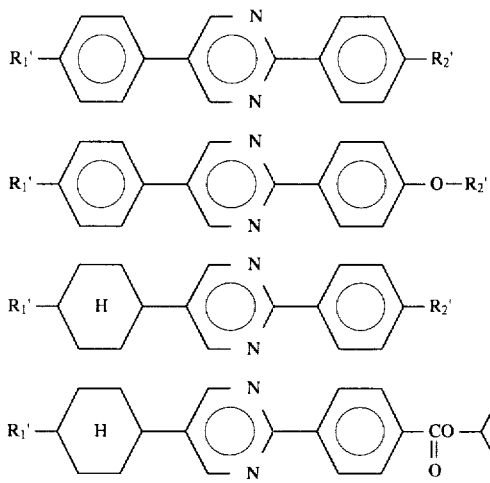
(IVaa)
(IVab)
(IVba)
(IVca)
(IVcb)
In the above-mentioned formulas (Va) and (Vb), more preferred compounds thereof may include those represented by the formulas (Vaa) to (Vbf):
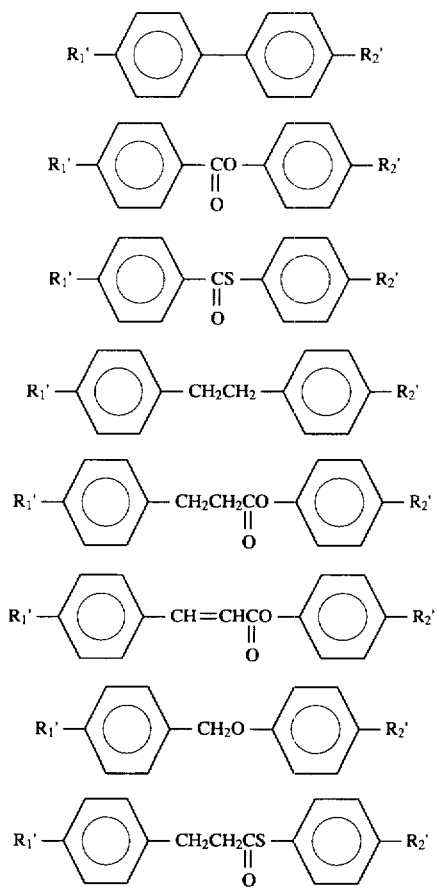
(Vaa)
(Vab)
(Vac)
(Vad)
(Vae)
(Vaf)
(Vag)
(Vah)
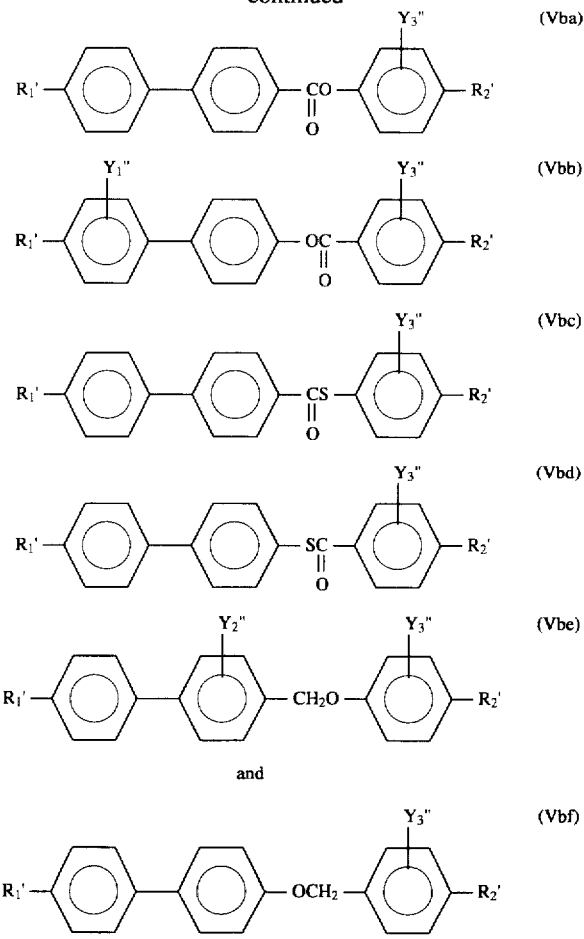
(Vba)
(Vbb)
(Vbc)
(Vbd)
(Vbe)
and
(Vbf)
In the above-mentioned formulas (VIa) to (VIf), more preferred compounds thereof may include those represented by the formulas (VIaa) to (VIfa):

(VIaa)

$R_1'$—[H]—OC(=O)—[⌬]—[⌬]—$R_2'$ (VIab)

$R_1'$—[H]—CH$_2$O—[⌬]—[⌬]—$R_2'$ (VIba)

$R_1'$—[H]—[H]—OC(=O)—[⌬]—$R_2'$ (VIbb)

$R_1'$—[H]—[H]—OCH$_2$—[⌬]—$R_2'$ (VIda)

$R_1'$—[H]—[⌬]—CO(=O)—[⌬]—$R_2'$ (VIea)

$R_1'$—[⌬]—[H]—CO(=O)—[⌬]—$R_2'$ and (VIfa)

$R_1'$—[H]—CO(=O)—[⌬]—$R_2'$ (VII)

$R_3'$—$X_1'$—[naphthalene]—($X_3'$—[⌬])$_E$—$X_2'$—$R_4'$ wherein E denotes 0 or 1; $X_1'$ and $X_2'$ respectively denote a single bond, $-\underset{\underset{O}{\|}}{C}O-, -O\underset{\underset{O}{\|}}{C}-, -O-$ or $-O\underset{\underset{O}{\|}}{C}O-$;

and $X_3'$ denotes a single bond $-\underset{\underset{O}{\|}}{C}O-, -O\underset{\underset{O}{\|}}{C}-, -CH_2O-$ or $-OCH_2-$.

(VIII)

$R_3'$—$X_1'$—[⌬]$_F$—$X_3'$—[pyridine]—$X_4'$—[⌬]$_G$—$X_2'$—$R_4'$ wherein F and G respectively denote 0 to 1; $X_1'$ and $X_2'$ respectively denote a single bond, $-\underset{\underset{O}{\|}}{C}O-, -O\underset{\underset{O}{\|}}{C}-$ or $-O-$;

and $X_3'$ and $X_4'$ respectively denote a single bond, $-\underset{\underset{O}{\|}}{C}O-, -O\underset{\underset{O}{\|}}{C}-, -CH_2O-$ or $-OCH_2-$.

In the above formula (VII), preferred compounds thereof may include those represented by the following formulas (VIIa) and (VIIb):

(VIIa)

$R_3'$—[naphthalene]—CO(=O)—[⌬]—$R_4'$, and (VIIb)

$R_3'$—[naphthalene]—OC(=O)—[⌬]—$R_4'$.

In the above formula (VIII), preferred compounds thereof may include those represented by the following formulas (VIIIa) and (VIIIb).

(VIIIa)

$R_3'$—[⌬]—[pyrazine]—$R_4'$, and (VIIIb)

$R_3'$—[⌬]—[pyrazine]—$X_1'$—[⌬]—$R_4'$.

More preferred compounds of the formula (VIIIb) may include those represented by the formulas (VIIIba) to (VIIIbb):

(VIIIba)

$R_3'$—[⌬]—[pyrazine]—CO(=O)—[⌬]—$R_4'$, and (VIIIbb)

$R_3'$—[⌬]—[pyrazine]—OC(=O)—[⌬]—$R_4'$.

Herein, $R_3'$ and $R_4'$ respectively denote a linear or branched alkyl group having 1–18 carbon atoms capable of including one or non-neighboring two or more methylene groups which can be replaced with —CH halogen—and capable of further including one or two or more non-neighboring methylene groups other than those directly connected to $X_1'$ or $X_2'$ which can be replaced with at least one species of

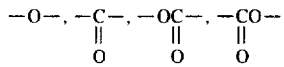

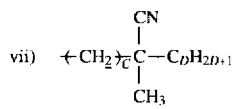

wherein C denotes an integer of 0–2 and D denotes an integer of 1–15 (optically active or inactive).

-continued

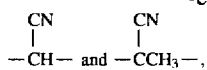

with proviso that $R_3'$ and $R_4'$ respectively do not connect to a ring structure by a single bond when $R_3'$ and $R_4'$ respectively denote a halogenated alkyl group containing one methylene group replaced with —CH halogen—.

Further, preferred examples of $R_3'$ and $R_4'$ may respectively include those represented by the following groups (i) to (vii):

i) a linear alkyl group having 1–15 carbon atoms;

ii) 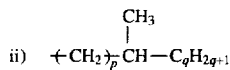

wherein p denotes an integer of 0–5 and q denotes an integer of 2–11 (optically active or inactive);

iii) 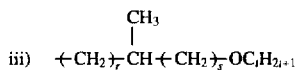

wherein r denotes an integer of 0–6, s denotes 0 or 1, and t denotes an integer of 1–14 (optically active or inactive);

iv) 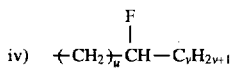

wherein u denotes an integer of 0 or 1 and v denotes an integer of 1–16 (optically active or inactive);

v) 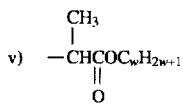

wherein w denotes an integer of 1–15 (optically active or inactive);

vi) 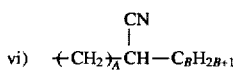

wherein A denotes an integer of 0–2 and B denotes an integer of 1–15 (optically active or inactive); and vii) 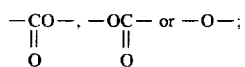

wherein C denotes an integer of 0–2 and D denotes an integer of 1–15 (optically active or inactive).

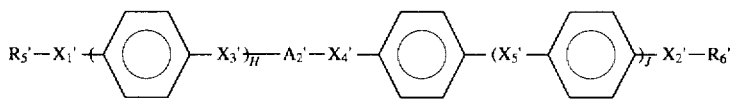

(IX)

wherein H and J respectively denote 0 or 1 with proviso that H+J=0 or 1 ; $X_1'$ and $X_2'$ respectively denote a single bond,

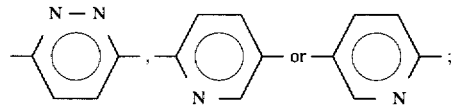

$A_2'$ denotes

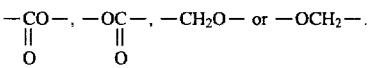

and $X_3'$ and $X_4'$ respectively denote a single bond,

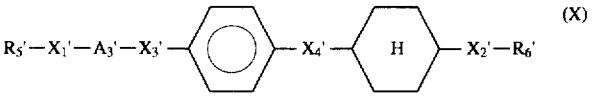

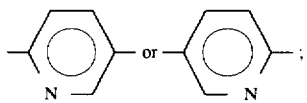

(X)

wherein $X_1'$ and $X_2'$ respectively denote a single bond,

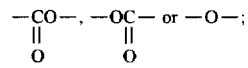

$A_3'$ denotes

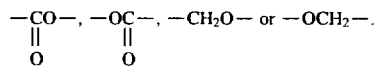

and $X_3'$ and $X_4'$ respectively denote a single bond,

—CO—, —OC—, —CH$_2$O— or —OCH$_2$—.
‖         ‖
O          O

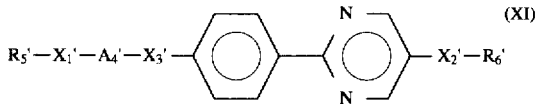

(XI)

wherein $X_1'$ and $X_2'$ respectively denote a single bond, $$-\underset{\underset{O}{\|}}{C}O-,\ -O\underset{\underset{O}{\|}}{C}-\ \text{or}\ -O-;$$

$A_4'$ denotes

[structure: pyridine rings]

and
$X_3'$ respectively denotes a single bond $$-\underset{\underset{O}{\|}}{C}O-,\ -O\underset{\underset{O}{\|}}{C}-,\ -CH_2O-\ \text{or}\ -OCH_2-.$$

(XII)

[structure showing: $R_5'$—[ring with $Y_4''$]$_K$—(C=N—N=C with S)—[ring with $Y_5''$]—$X_3'$—[ring with $Y_6''$]$_L$—[H]$_M$—$X_1'$—$R_6'$]

wherein K, L and M respectively denote 0 or 1 with the proviso that K+L+M =0 or 1 ; $X_1'$ denotes a single bond, $$-\underset{\underset{O}{\|}}{C}O-,\ -O\underset{\underset{O}{\|}}{C}-\ \text{or}\ -O-;$$

$X_3'$ denotes a single bond, $$-\underset{\underset{O}{\|}}{C}O-,\ -O\underset{\underset{O}{\|}}{C}-,\ -CH_2O-\ \text{or}\ -OCH_2-;$$

and $Y_4''$, $Y_5''$ and $Y_6''$ respectively denote H or F.

In the above formula (IX), preferred compounds thereof may include those represented by the following formulas (IXa) to (IXc):

(IXa) $R_5'—X_2'—A_2'$—[ring]—$X_2'—R_6'$, (IXb) $R_5'—X_1'—A_2'$—[ring]—$X_5'$—[ring]—$X_2'—R_6'$, and (IXc) $R_5'—X_1'$—[ring]—$A_2'$—[ring]—$X_2'—R_6'$.

In the above formula (X), preferred compounds thereof may include those represented by the following formulas (Xa) and (Xb):

(Xa) $R_5'—X_1'—A_3'$—[ring]—$X_4'$—[H]—$X_2'—R_6'$, and

-continued (Xb) $R_5'—X_1'—A_3'—X_3'$—[ring]—[H]—$X_2'—R_6'$.

In the above formula (XII), preferred compounds thereof may include those represented by the following formulas (XIIa) and (XIId):

(XIIa) $R_5'$—[ring with $Y_4''$]—(C=N—N=C with S)—[ring with $Y_5''$]—$X_1'—R_6'$ (XIIb) $R_5'$—(C=N—N=C with S)—[ring with $Y_5''$]—$X_1'—R_6'$ (XIIc) $R_5'$—(C=N—N=C with S)—[ring with $Y_5''$]—$X_3'$—[ring with $Y_6''$]—$X_1'—R_6'$, and (XIId) $R_5'$—(C=N—N=C with S)—[ring with $Y_5''$]—$X_3'$—[H]—$X_1'—R_6'$.

In the above-mentioned formulas (IXa) to (IXc), more preferred compounds thereof may include those represented by the formulas (IXaa) to (IXcc):

(IXaa) $R_5'—A_2'$—[ring]—$R_6'$, (IXab) $R_5'—A_2'$—[ring]—$OR_6'$, (IXac) $R_5'—A_2'$—[ring]—$OCR_6'$,
$\underset{\underset{O}{\|}}{}$

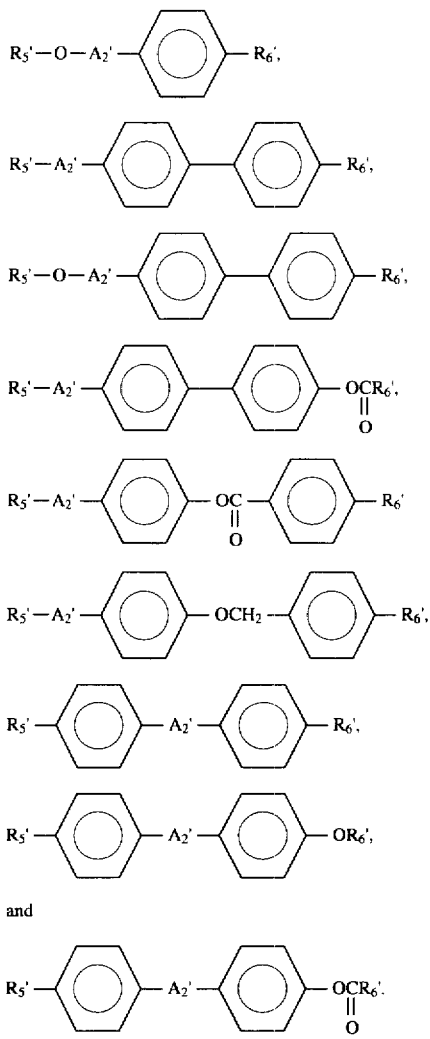

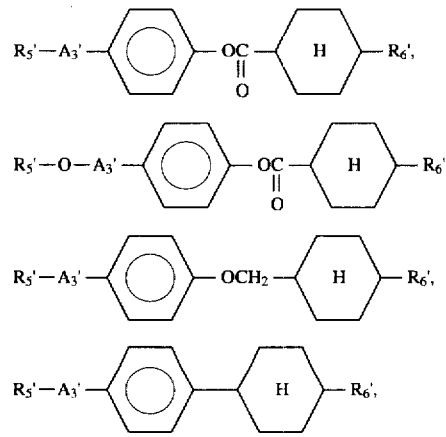

and

In the above-mentioned formulas (Xa) to (Xb), more preferred compounds thereof may include those represented by the formulas (Xaa) to (Xbb):

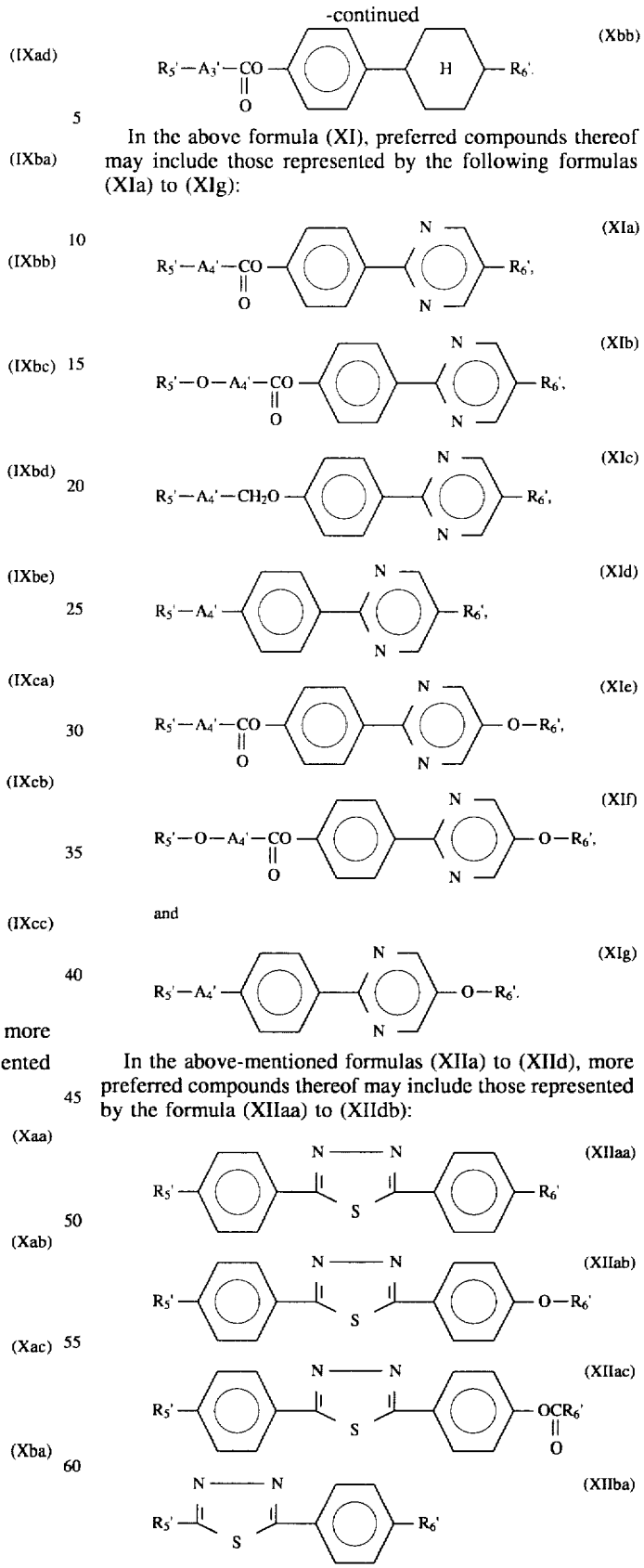

In the above formula (XI), preferred compounds thereof may include those represented by the following formulas (XIa) to (XIg):

In the above-mentioned formulas (XIIa) to (XIId), more preferred compounds thereof may include those represented by the formula (XIIaa) to (XIIdb):

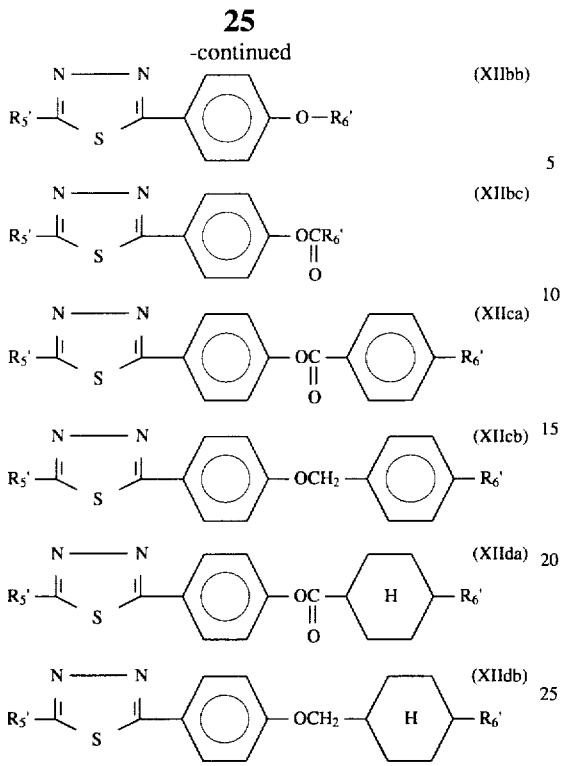

Herein, $R_5'$ and $R_6'$ respectively denote a linear or branched alkyl group having 1–18 carbon atoms capable of including one non-neighboring two or more methylene groups other than those directly connected to $X_1'$ or $X_2'$ which can be replaced with at least one species of $$-O-,\ -\underset{\underset{O}{\|}}{C}-,\ -\underset{\underset{O}{\|}}{O C}-,\ -\underset{\underset{O}{\|}}{C O}-,$$

$$-\underset{\underset{CN}{|}}{CH}-\ \text{and}\ -\underset{\underset{CN}{|}}{CCH_3}-.$$

Further, preferred examples of $R_5'$ and $R_6'$ may respectively include those represented by the following groups (i) to (vi):

i) a linear alkyl group having 1–15 carbon atoms;

ii) 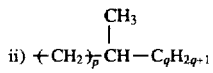

wherein p denotes an integer of 0–5 and q denotes an integer of 2–11 (optically active or inactive);

iii) 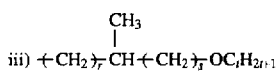

wherein r denotes an integer of 0–6, s denotes 0 or 1, and t denotes an integer of 1–14 (optically active or inactive);

iv) 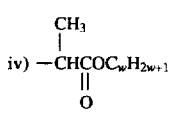

wherein w denotes an integer of 1–15 (optically active or inactive);

v) $+CH_2\overline{)_A}CH-C_BH_{2B+1}$
   |
   CN wherein A denotes an integer of 0–2 and B denotes an integer of 1–15 (optically active or inactive); and vi) $+CH_2\overline{)_C}C-C_DH_{2D+1}$
   | |
   CN CH_3 wherein C denotes an integer of 0–2 and D denotes an integer of 1–15 (optically active or inactive).

In the above mesomorphic compounds of the formulae (III) to (XII), (IIIa) to (XIId) and (IIIaa) to (XIIdb), at least one terminal group (i.e., $R_1'$ and/or $R_2'$, $R_3'$ and/or $R_4'$, or $R_5'$ and/or $R_6'$) may be the group: $(CH_2)_E C_G F_{2G+1}$ in which E is an integer of 0–10 and G is an integer of 1–15.

In the present invention, mesomorphic compounds represented by the following formulae (XIII) to (XVIII) may also be used as another mesomorphic compound.

Specific examples of another mesomorphic compound may also include those represented by the following formulae (XIII) to (XVIII) including abbreviations for respective cyclic groups listed below in addition to those described above.

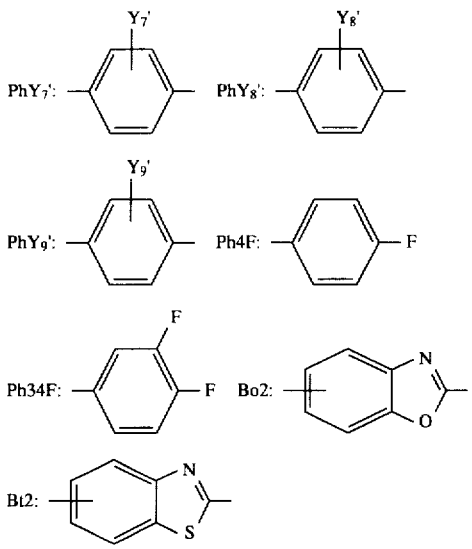

| | |
|---|---|
| $R_7'$—(Py2)—$X_7'$—(Ph)—$X_8'$—(PhY$_7'$)$_N$—(Tn)—$R_8'$ | (XIII) |
| $R_7'$—(Py2)—(Ph)—OCO—(Ph4F) | (XIV) |
| $R_7'$—(Py2)—(Ph)—OCO—(Ph34F) | (XV) |
| $R_7'$—(PhY$_7'$)$_Q$—(Tz1)—(PhY$_8'$)—$X_7'$—(PhY$_9'$)$_R$—(CY)$_T$—$R_8'$ | (XVI) |
| $R_7'$—(Bo2)—$A_4'$—$R_8'$ | (XVII) |
| $R_7'$—(Bt2)—$A_4'$—$R_8'$ | (XVIII) |

Herein, $R_7'$ and $R_8'$ respectively denote hydrogen or a linear or branched alkyl group having 1–18 carbon atoms capable of including one or non-neighboring two or more methylene groups which can be replaced with —O—, —CO—, —CH(CN)—or —CCH$_3$(CN)—provided that heteroatoms are not adjacent to each other and capable of including at least one H which can be replaced with F.

Further, preferred examples of $R_7'$ and $R_8'$ may respectively include those represented by the following groups (i) to (viii):

i) a linear alkyl group having 1–15 carbon atoms;

ii) 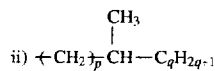

wherein p denotes an integer of 0–5 and q denotes an integer of 2–11 (optically active or inactive);

iii) 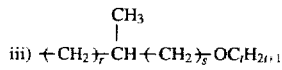

wherein r denotes an integer of 0–6, s denotes 0 or 1, and t denotes an integer of 1–14 (optically active or inactive);

iv) 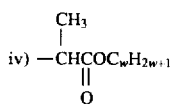

wherein w denotes an integer of 1–15 (optically active or inactive);

v) 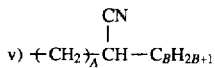

wherein A denotes an integer of 0–2 and B denotes an integer of 1–15 (optically active or inactive);

vi) 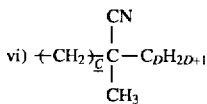

wherein C denotes an integer of 0–2 and D denotes an integer of 1–15 (optically active or inactive);

vii) —(CH$_2$)—$_E$ C$_G$F$_{2G+1}$ wherein E is an integer of 0–10 and G is an integer of 1–15; and viii) H (hydrogen).

In the above formulae (XIII) to (XVIII); N, Q, R and T are 0 or 1 ; $Y_7'$, $Y_8'$ and $Y_9'$ are H or F; $A_4'$ is Ph or Np; and $X_7'$ and $X_8'$ respectively denote a single bond, —COO—, —OCO—, —CH$_2$O— or —OCH$_2$—.

The compound of the formula (XIII) may preferably include a compound represented by the following formula (XIIIa):

$R_7'$—(Py2)—(Ph)—OCO—(Tn)—$R_8'$    (XIIIa).

The compound of the formula (XVI) may preferably include compounds represented by the following formulae (XVIa) and (XVIb):

$R_7'$—(Tz1)—(Ph)—$R_8'$    (XVIa), and $R_7'$—(PhY$_7'$)—(Tz1)—(PhY$_8'$)—$R_8'$    (XVIb).

The compound of the formula (XVII) may preferably include compounds represented by the following formulae (XVIIa) and (XVIIb):

$R_7'$—(Boa2)—(Ph)—O—$R_8'$    (XVIIa), and $R_7'$—(Boa2)—(Np)—O—$R_8'$    (XVIIb).

The compounds of the formula (XVIII) and may preferably include compounds represented by the The compounds of the formula (XVIa) and following formulae (XVIIIa) to (XVIIIc):

$R_7'$—(Btb2)—(Ph)—$R_8'$    (XVIIIa), $R_7'$—(Btb2)—(Ph)—O—$R_8'$    (XVIIIb), and $R_7'$—(Btb2)—(Np)—O—$R_8'$    (XVIIIc).

The compounds of the formula (XVIa) and (XVIb) may preferably include compounds represented by the following formulae (XVIa) to (XVIc):

$R_7'$—(Tz1)—(Ph)—O—$R_8'$    (XVIaa), $R_7'$—(Ph)—(Tz1)—(Ph)—$R_8'$    (XVIba), $R_7'$—(Ph)—(Tz1)—(Ph)—O—$R_8'$    (XVIbb), and $R_7'$—(Ph)—(Tz1)—(Ph)—OCO—$R_8'$    (XVIbc).

In formulating the liquid crystal composition according to the present invention, the liquid crystal composition may desirably contain 1–80 wt. %, preferably 1–60 wt. %, more preferably 1–40 wt. % of a mesomorphic compound represented by the formula (I) (optically active or inactive).

Further, when two or more species of the mesomorphic compounds represented by the formula (I) are used, the liquid crystal composition may desirably contain 1–80 wt. %, preferably 1–60 wt. %, more preferably 1–40 wt. %, of the two or more species of the mesomorphic compounds represented by the formula (I) (optically active or inactive).

The liquid crystal device according to the present invention may preferably be prepared by heating the liquid crystal composition as prepared above into an isotropic liquid under vacuum, filling a blank cell comprising a pair of oppositely spaced electrode plates with the composition, gradually cooling the cell to form a liquid crystal layer and restoring the normal pressure.

FIG. 1 is a schematic sectional view of an embodiment of the liquid crystal device utilizing ferroelectricity as prepared above for explanation of the structure thereof.

Referring to FIG. 1, the liquid crystal device includes a liquid crystal layer 1 assuming a chiral smectic phase disposed between a pair of glass substrates 2 each having thereon a transparent electrode 3 and an insulating alignment control layer 4. In the present invention, the transparent electrode 3 may be formed on one of the substrates 2. The glass substrates 2 are placed or arranged opposite each other. Lead wires 6 are connected to the electrodes so as to apply a driving voltage to the liquid crystal layer 1 from a power supply 7. Outside the substrates 2, a pair of polarizers 8 are disposed so as to modulate incident light $I_O$ from a light source 9 in cooperation with the liquid crystal 1 to provide modulated light 1.

Each of two glass substrates 2 is coated with a transparent electrode 3 comprising a film of In$_2$O$_3$, SnO$_2$ or ITO (indium-tin-oxide) to form an electrode plate. Further thereon, an insulating alignment control layer 4 is formed by rubbing a film of a polymer such as polyimide with gauze or acetate fiber-planted cloth so as to uniaxially align the liquid crystal molecules in the rubbing direction (uniaxial alignment treatment). Further, it is also possible to compose the alignment control layer 4 of two layers, e.g., by first forming an insulating layer of an inorganic material, such as silicon nitride, silicon carbide containing hydrogen, silicon oxide, boron nitride, boron nitride containing hydrogen, cerium oxide, aluminum oxide, zirconium oxide, titanium oxide, or magnesium fluoride, and forming thereon an alignment control layer of an organic insulating material, such as polyvinyl alcohol, polyimide, polyamide-imide, polyester-imide, polyparaxylylene, polyester, polycarbonate, polyvinyl acetal, polyvinyl chloride, polyvinyl acetate, polyamide, polystyrene, cellulose resin, melamine resin, urea resin, acrylic resin, or photoresist resin. Alternatively, it is also possible to use a single layer of inorganic insulating alignment control layer comprising the above-mentioned inorganic material or organic insulating alignment control layer comprising the above-mentioned organic material. An inorganic insulating alignment control layer may be formed by vapor deposition, while an organic insulating alignment control layer may be formed by applying a solution of an organic insulating material or a precursor thereof in a concentration of 0.1 to 20 wt. %, preferably 0.2–10 wt. %, by spinner coating, dip coating, screen printing, spray coating or roller coating, followed by curing or hardening under prescribed hardening condition (e.g., by heating). The insulating alignment control layer 4 may have a thickness of ordinarily 10 Å–1 micron, preferably 10–3000 Å, further preferably 10–1000 Å. The two glass substrates 2 with transparent electrodes 3 (which may be inclusively referred to herein as "electrode plates") and further with insulating alignment control layers 4 thereof are held to have a prescribed (but arbitrary) gap with a spacer 5. For example, such a cell structure with a prescribed gap may be formed by sandwiching spacers of silica beads or alumina beads having a prescribed diameter with two glass plates, and then sealing the periphery thereof with, a sealing material comprising, e.g., an epoxy adhesive. Alternatively, a polymer film or glass fiber may also be used as a spacer. Between the two glass plates, a liquid crystal composition assuming a chiral smectic phase is sealed up to provide a liquid crystal layer 1 in a thickness of generally 0.5 to 20 μm, preferably 1 to 5 μm.

The transparent electrodes 3 are connected to the external power supply 7 through the lead wires 6. Further, outside the glass substrates 2, a pair of polarizers 8 arranged in, e.g., right angle cross nicol relationship are applied. The device shown in FIG. 1 is of a transmission type and accordingly is provided with a light source 9 at the back of one of the polarizers 8.

Figure 2:
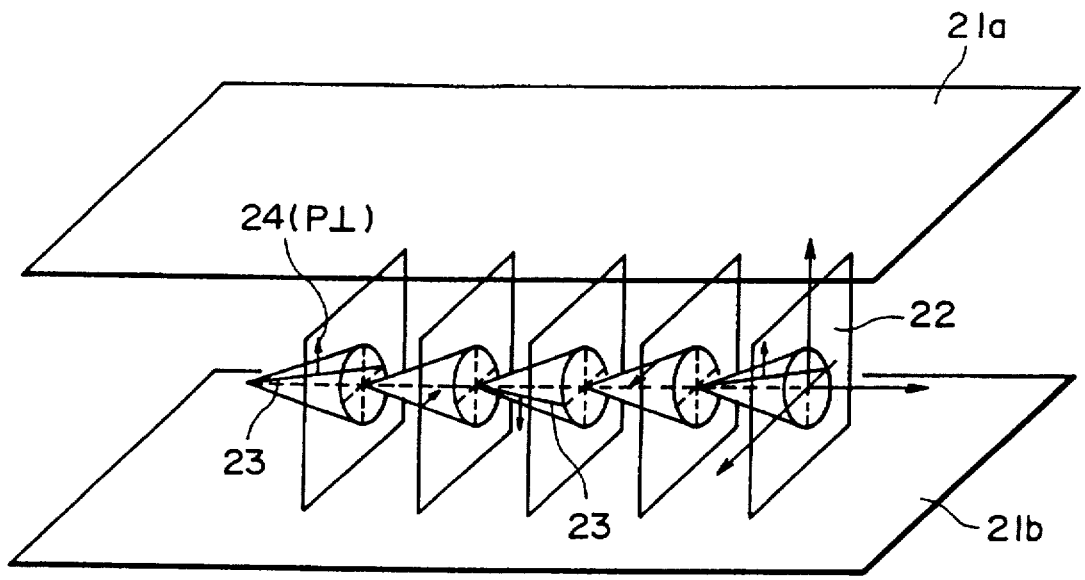
FIGS. 2 and 3 are schematic perspective views of a device cell embodiment for illustrating the operation principle of a liquid crystal device utilizing ferroelectricity of a liquid crystal composition.

FIG. 2 is a schematic illustration of a liquid crystal cell (device) utilizing ferroelectricity for explaining operation thereof. Reference numerals 21a and 21b denote substrates (glass plates) on which a transparent electrode of, e.g., $In_2O_3$, $SnO_2$, ITO (indium-tin-oxide), etc., is disposed, respectively. A liquid crystal of an SmC*-phase (chiral smectic C phase) or SmH*-phase (chiral smectic H phase) in which liquid crystal molecular layers 22 are aligned perpendicular to surfaces of the glass plates is hermetically disposed therebetween. Lines 23 show liquid crystal molecules. Each liquid crystal molecule 23 has a dipole moment (P⊥) 24 in a direction perpendicular to the axis thereof. The liquid crystal molecules 23 continuously form a helical structure in the direction of extension of the substrates. When a voltage higher than a certain threshold level is applied between electrodes formed on the substrates 21a and 21b, a helical structure of the liquid crystal molecule 23 is unwound or released to change the alignment direction of respective liquid crystal molecules 23 so that the dipole moments (P⊥) 24 are all directed in the direction of the electric field. The liquid crystal molecules 23 have an elongated shape and show refractive anisotropy between the long axis and the short axis thereof. Accordingly, it is easily understood that when, for instance, polarizers arranged in a cross nicol relationship, i.e., with their polarizing directions crossing each other, are disposed on the upper and the lower surfaces of the glass plates, the liquid crystal cell thus arranged functions as a liquid crystal optical modulation device of which optical characteristics vary depending upon the polarity of an applied voltage.

Figure 3:
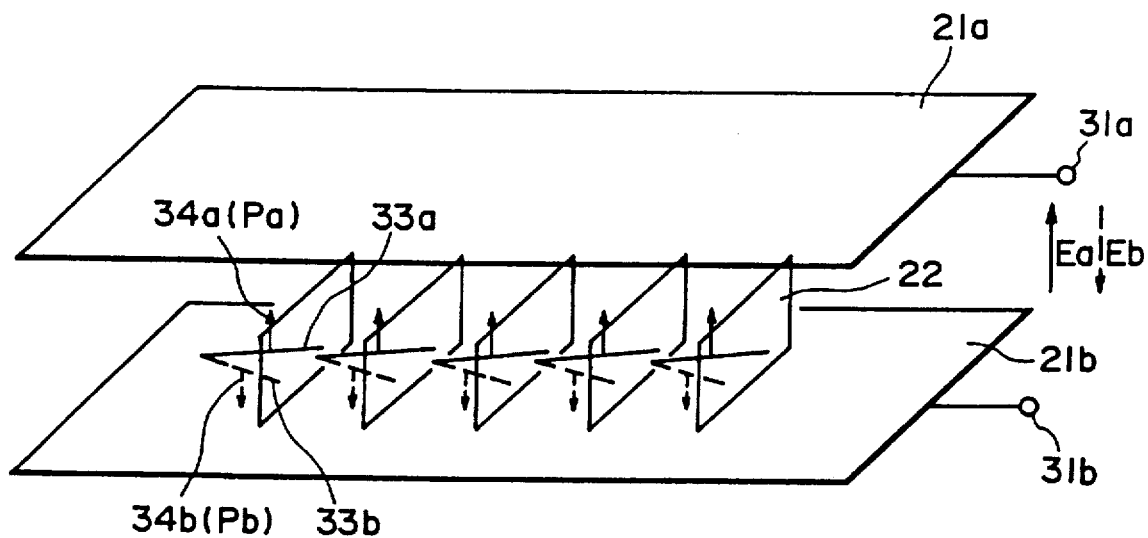
Figure 4:
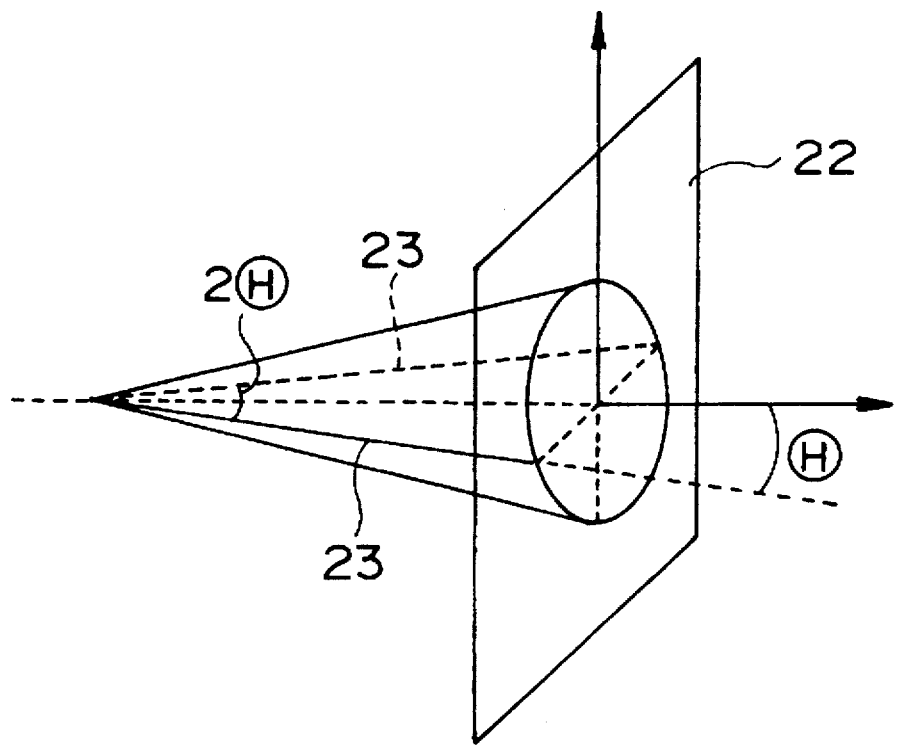
FIG. 4 is a schematic view for illustrating a tilt angle Ĥ in a ferroelectric liquid crystal with a helical structure.

Further, when the liquid crystal cell is made sufficiently thin (e.g., less than about 10 microns), the helical structure of the liquid crystal molecules is unwound to provide a non-helical structure even in the absence of an electric field, whereby the dipole moment assumes either of the two states, i.e., Pa in an upper direction 34a or Pb in a lower direction 34b as shown in FIG. 3, thus providing a bistable condition. When an electric field Ea or Eb higher than a certain threshold level and different from each other in polarity as shown in FIG. 3 is applied to a cell having the above-mentioned characteristics by using voltage application means 31a and 31b, the dipole moment is directed either in the upper direction 34a or in the lower direction 34b depending on the vector of the electric field Ea or Eb. In correspondence with this, the liquid crystal molecules are oriented in either of a first stable state 33a and a second stable state 33b.

When the above-mentioned ferroelectric liquid crystal is used as an optical modulation element, it is possible to obtain two advantages. First is that the response speed is quite fast. Second is that the orientation of the liquid crystal shows bistability. The second advantage will be further explained, e.g., with reference to FIG. 3. When the electric field Ea is applied to the liquid crystal molecules, they are oriented in the first stable state 33a. This state is stably retained even if the electric field is removed. On the other hand, when the electric field Eb of which direction is opposite to that of the electric field Ea is applied thereto, the liquid crystal molecules are oriented to the second stable state 33b, whereby the directions of molecules are changed. This state is similarly stably retained even if the electric field is removed. Further, as long as the magnitude of the electric field Ea or Eb being applied is not above a certain threshold value, the liquid crystal molecules are placed in the respective orientation states.

Figure 5A:
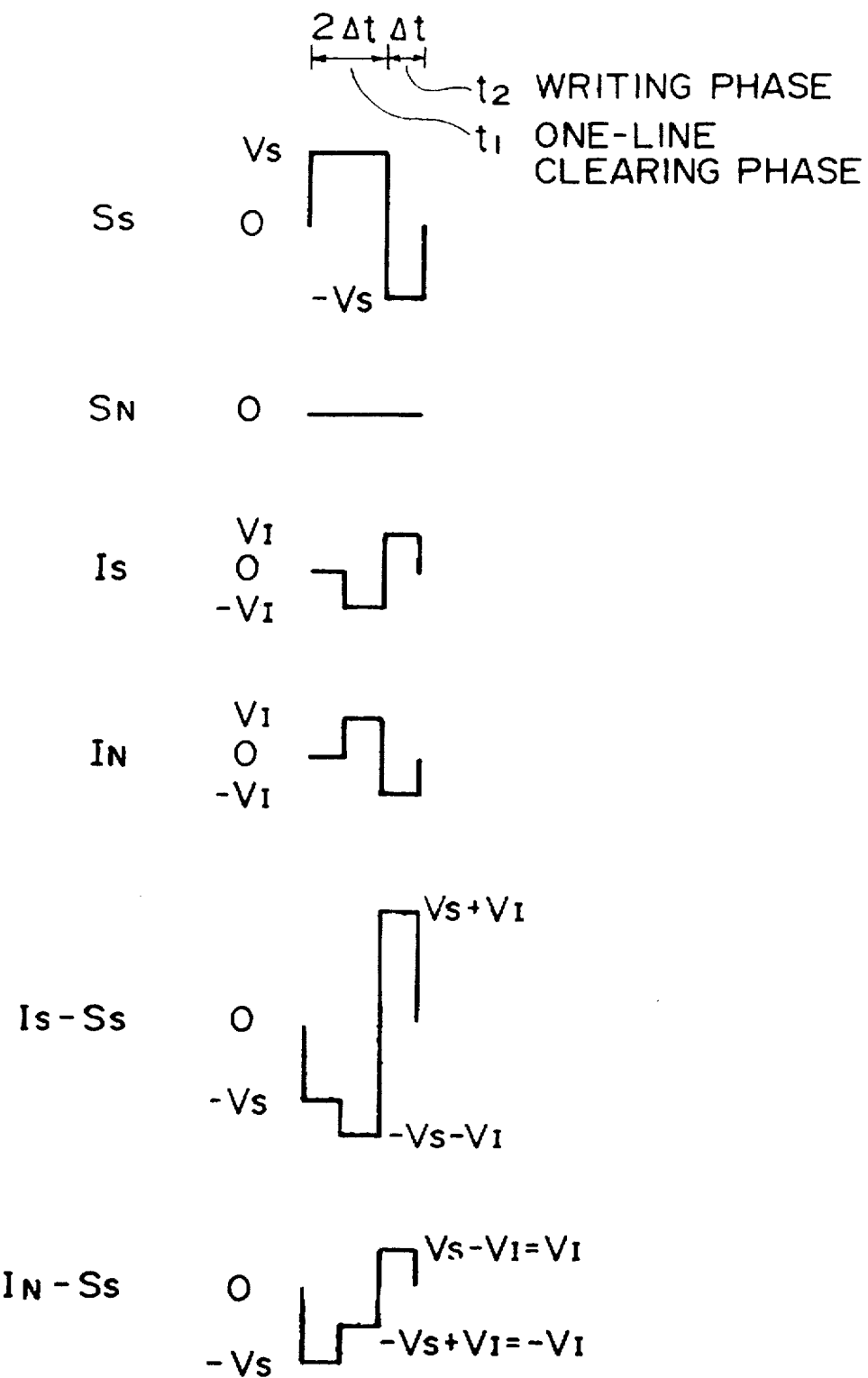
FIG. 5A shows unit driving waveforms used in an embodiment of the present invention.
Figure 5B:
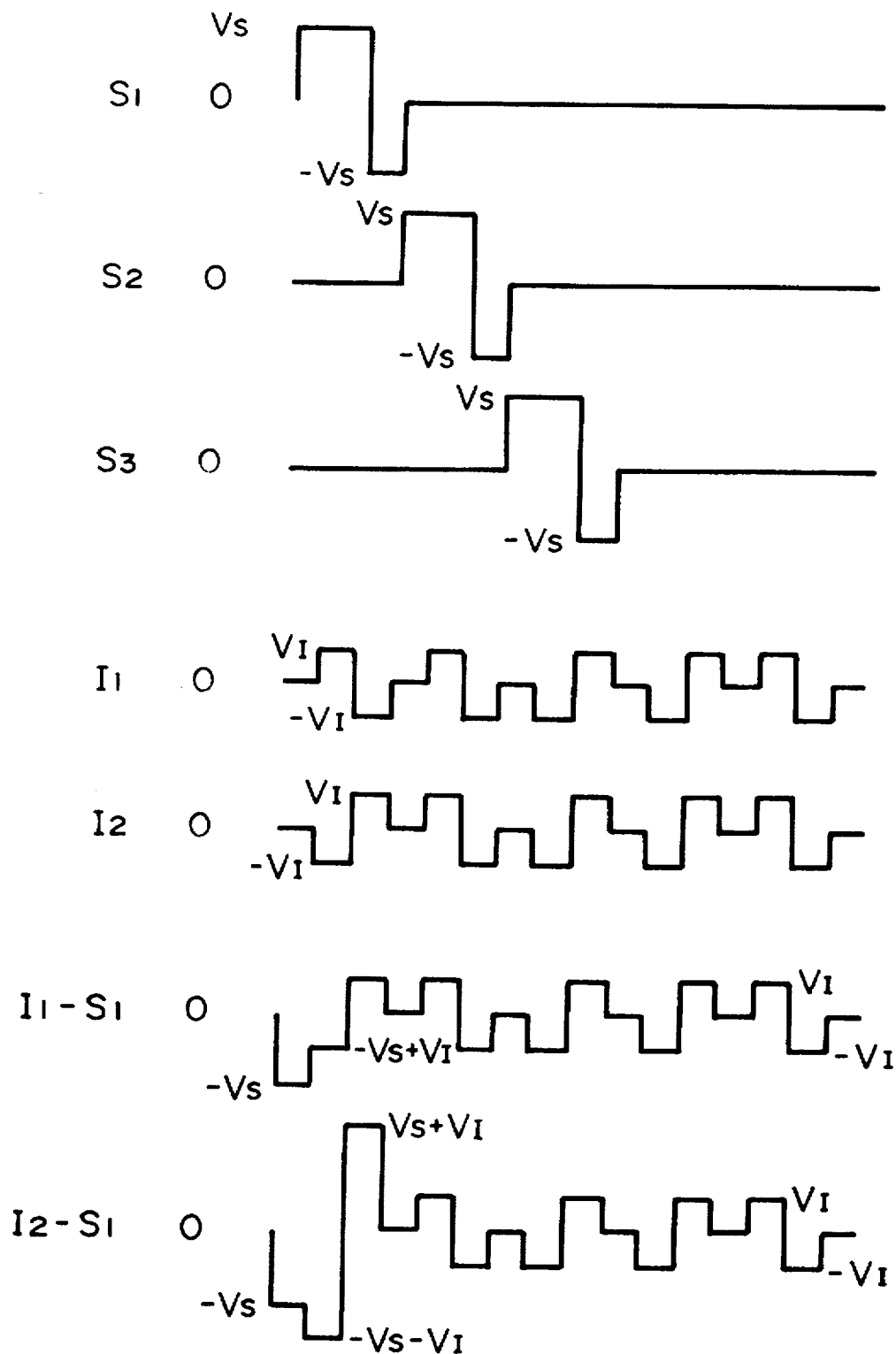
FIG. 5B is time-serial waveforms comprising a succession of such unit waveforms.

FIGS. 5A and 5B are waveform diagrams showing driving voltage waveforms adopted in driving a ferroelectric liquid crystal panel as an embodiment of the liquid crystal device according to the present invention.

Referring to FIG. 5A, at $S_S$ is shown a selection scanning signal waveform applied to a selected scanning line, at $S_N$ is shown a non-selection scanning signal waveform applied to a non-selected scanning line, at $I_S$ is shown a selection data signal waveform (providing a black display state) applied to a selected data line, and at $I_N$ is shown a non-selection data signal waveform (providing a white display state) applied to a non-selected data line. Further, at $(I_S\text{-}S_S)$ and $(I_N\text{-}S_S)$ in the figure are shown voltage waveforms applied to pixels on a selected scanning line, whereby a pixel supplied with the voltage $(I_S\text{-}S_S)$ assumes a black display state and a pixel supplied with the voltage $(I_N\text{-}S_S)$ assumes a white display state. FIG. 5B shows a time-serial waveform used for providing a display state as shown in FIG. 6.

In the driving embodiment shown in FIGS. 5A and 5B, a minimum duration $\Delta t$ of a single polarity voltage applied to a pixel on a selected scanning line corresponds to the period of a writing phase $t_2$, and the period of a one-line clearing phase $t_1$ is set to $2\Delta t$.

The parameters $V_S$, $V_I$ and $\Delta t$ in the driving waveforms shown in FIGS. 5A and 5B are determined depending on switching characteristics of a ferroelectric liquid crystal material used. In this embodiment, the parameters are fixed at a constant value of a bias ratio $V_I/(V_I+V_S)=\frac{1}{3}$. It is of course possible to increase a range of a driving voltage allowing an appropriate matrix drive by increasing the bias ratio. However, a large bias ratio corresponds to a large amplitude of a data signal and leads to an increase in flickering and a lower contrast, thus being undesirable in respect of image quality. According to our study, a bias ratio of about $\frac{1}{5}$–$\frac{1}{4}$ was practical.

The liquid crystal device according to the present invention is used as an element, particularly a display element, for various liquid crystal apparatus.

Figure 7:
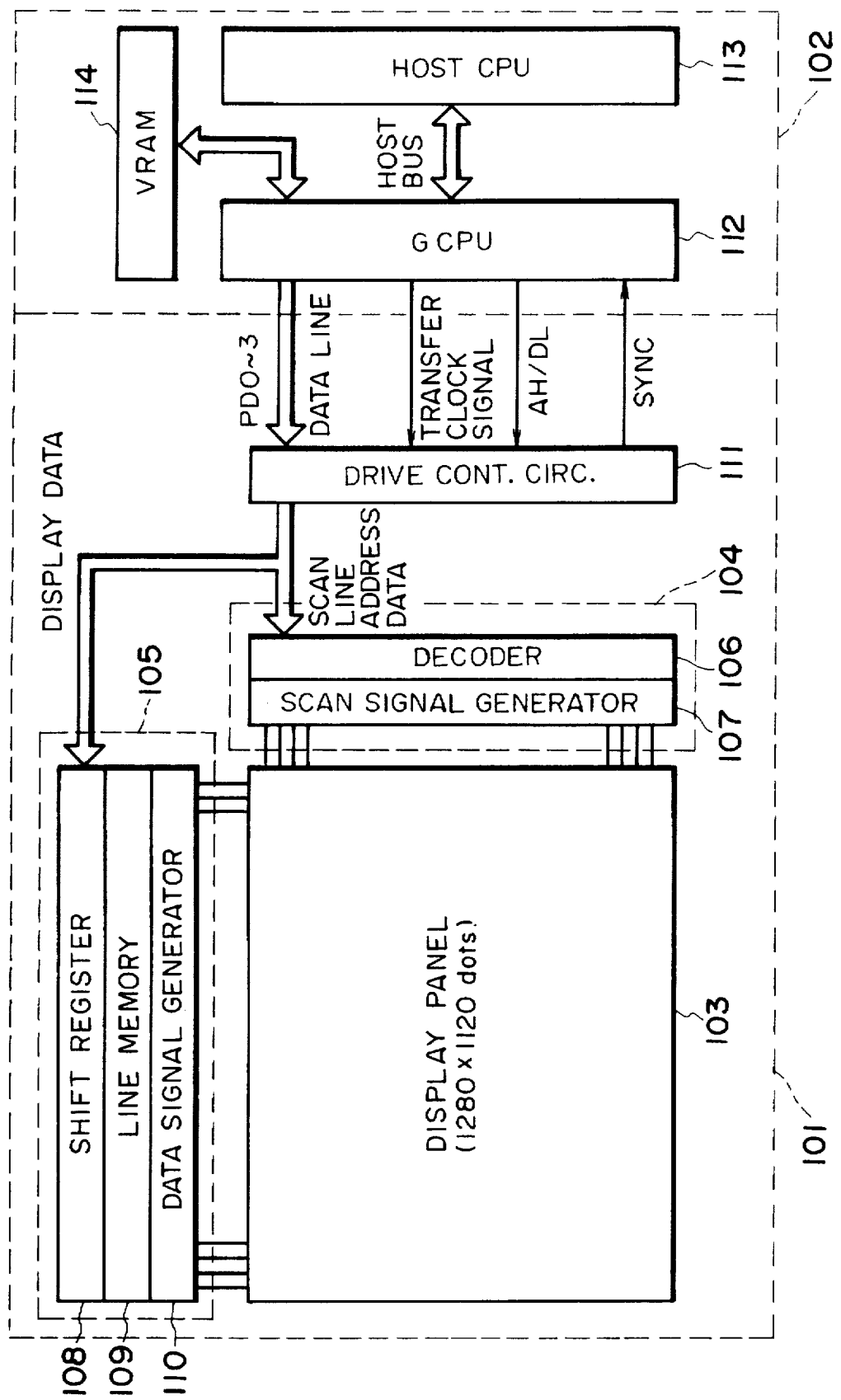
FIG. 7 is a block diagram showing a display apparatus comprising a liquid crystal device utilizing ferroelectricity of a liquid crystal composition and a graphic controller.
Figure 8:
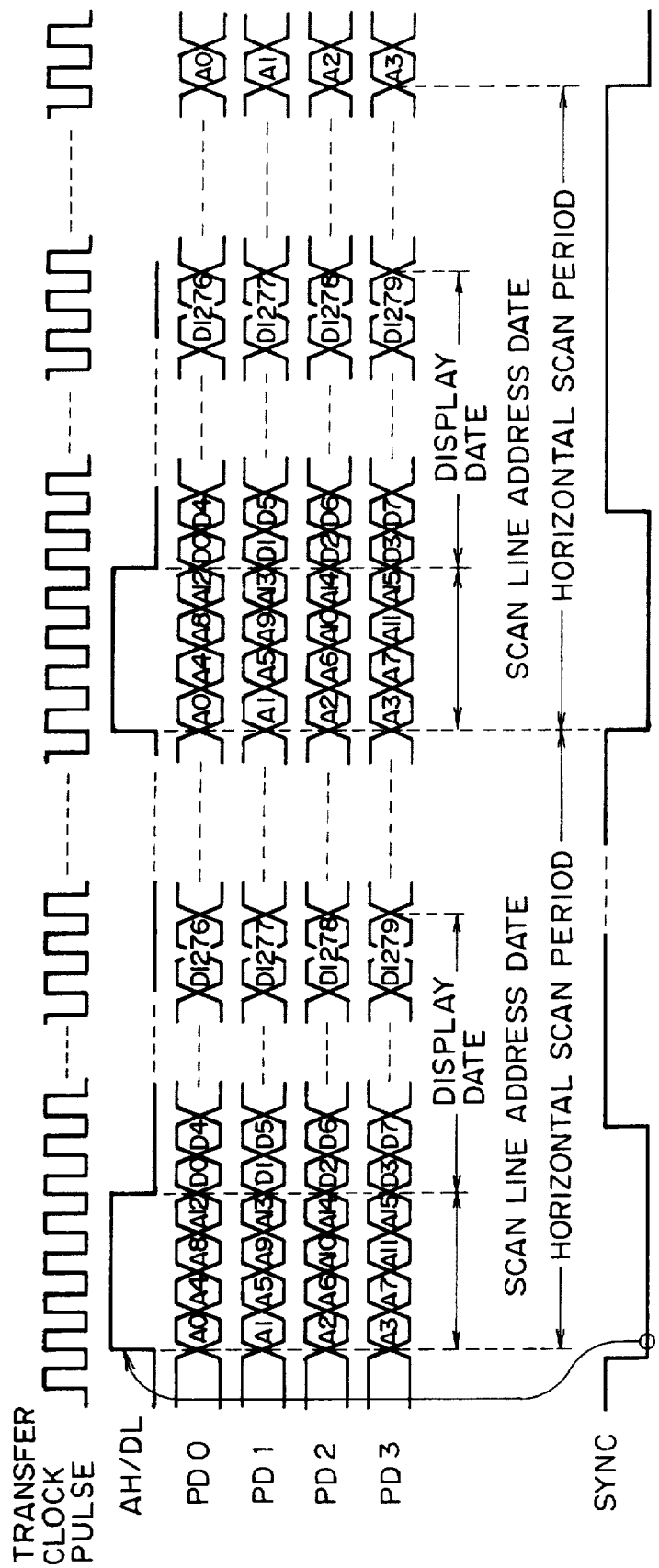
FIG. 8 is a time chart of image data communication showing time correlation between signal transfer and driving with respect to a liquid crystal display apparatus and a graphic controller.

Based on an arrangement appearing hereinbelow and data format comprising image data accompanied with scanning line address data and by adopting communication synchronization using a SYNC signal as shown in FIGS. 7 and 8, there is provided a liquid crystal display apparatus of the present invention which uses the liquid crystal device according to the present invention as a display panel portion.

Referring to FIG. 7, the ferroelectric liquid crystal display apparatus 101 includes a graphic controller 102, a display panel 103, a scanning line drive circuit 104, a data line drive circuit 105, a decoder 106, a scanning signal generator 107, a shift resistor 108, a line memory 109, a data signal generator 110, a drive control circuit 111, a graphic central processing unit (GCPU) 112, a host central processing unit (host CPU) 113, and an image data storage memory (VRAM) 114.

Image data are generated in the graphic controller 102 in an apparatus body and transferred to a display panel 103 by signal transfer means. The graphic controller 102 principally comprises a CPU (central processing unit, hereinafter referred to as "GCPU") 112 and a VRAM (video-RAM, image data storage memory) 114 and is in charge of management and communication of image data between a host CPU 113 and the liquid crystal display apparatus (FLCD) 101. The control of the display apparatus is principally performed by the graphic controller 102. A light source (not shown) is disposed at the back of the display panel 103.

Hereinbelow, the present invention will be explained more specifically with reference to examples. It is however to be understood that the present invention is not restricted to these examples.

EXAMPLE 1

Production of 2-(4-perfluorohexylphenyl)-5-nonylpyrimidine (Example Compound No. (34))

2.0 g (5.54 mM) of 2-(4-bromophenyl)-5-nonylpyrimidine, 2.11 g (33.2 mM) of copper powder and 12 ml of dimethyl sulfoxide (DMSO) were placed in a 30 ml-reaction vessel. To the mixture, a solution of 2.72 g (6.10 mM) of perfluorohexyl iodide in 2 ml of DMSO in 40 minutes at 105° C. under argon atmosphere, followed by stirring for 6 hours at 110° C. After the reaction, the reaction mixture was cooled and poured into 30 ml of water and then was subjected to extraction with ethyl acetate (20 ml×3 times). The resultant organic layer was washed with water and dried with anhydrous magnesium sulfate, followed by distilling-off of the solvent to obtain 2.5 g of a crude product.

The crude product was purified by silica gel column chromatography (eluent: hexane/toluene=$\frac{3}{1}$) to obtain 1.67 g of 2-(4-perfluorohexylphenyl)-5-nonylpyrimidine (Yield: 50%, melting point (m.p.): 84° C.).

EXAMPLE 2

Production of 2-(4-perfluorooctylphenyl)-5-nonylpyrimidine (Ex. Comp. No. (47))

2.0 9 (5.54 mM) of 2-(4-bromophenyl)-5-nonylpyrimidine, 2.11 g (33.2 mM) of copper powder and 12 ml of DMSO were placed in a 30 ml-reaction vessel. To the mixture, a solution of 3.33 g (6.10 mM) of perfluorooctyl iodide in 3 ml of DMSO in 30 minutes at 105° C. under argon atmosphere, followed by stirring for 5 hours at 120° C. After the reaction, the reaction mixture was cooled and poured into 30 ml of water and then was subjected to extraction with ethyl acetate (20 ml×3 times). The resultant organic layer was washed with water and dried with anhydrous magnesium sulfate, followed by distilling-off of the solvent to obtain 1.65 g of a crude product.

The crude product was purified by silica column chromatography (eluent: hexane/toluene=$\frac{3}{1}$) to obtain 1.67 g of 2-(4-perfluorooctylphenyl)-5-nonylpyrimidine (Yield: 36%, m.p.: 102° C.).

EXAMPLE 3

Production of 2-(4-perfluorohexylphenyl)-5-undecylpyrimidine (Ex. Comp. No. (44))

3.97 g (10.2 mM) of 2-(4-bromophenyl)-5-undecylpyrimidine, 3.89 g (61.3 mM) of copper powder and 25 ml of DMSO were placed in a 50 ml-reaction vessel. To the mixture, a solution of 5.0 g (11.2 mM) of perfluorohexyl iodide in 5 ml of DMSO in 25 minutes at 105° C. under argon atmosphere, followed by stirring for 6 hours at 115° C. After the reaction, the reaction mixture was cooled and poured into 50 ml of water and then was subjected to extraction with ethyl acetate (20 ml×3 times). The resultant organic layer was washed with water and dried with anhydrous magnesium sulfate, followed by distilling-off of the solvent to obtain 5.7 g of a crude product.

The crude product was purified by silica gel column chromatography (eluent: hexane/toluene=$\frac{3}{1}$) to obtain 2.14 g of 2-(4-perfluorohexylphenyl)-5-undecylpyrimidine (Yield: 50%).

Phase transition temperature (°C.)

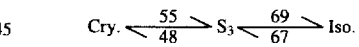

The respective symbols denote the following phases; Iso: isotropic phase; $S_3$: smectic phase (unidentified); and Cry.: crystal.

EXAMPLE 4

Production of 2-(4-perfluorooctylphenyl)-5-decyloxypyrimidine (Ex. Comp. No. (42))

2.5 g (6.40 mM) of 2-(4-bromophenyl)-5-decyloxypyrimidine, 2.45 g (38.6 mM) of copper powder and 15 ml of DMSO were placed in a 30 ml-reaction vessel. To the mixture, a solution of 3.85 g (7.5 mM) of perfluorooctyl iodide in 3 ml of DMSO in 30 minutes at 110° C. under argon atmosphere, followed by stirring for 8 hours at 120° C. After the reaction, the reaction mixture was cooled and poured into 30 ml of water and then was subjected to extraction with toluene (20 ml×3 times). The resultant organic layer was washed with water and dried with anhydrous magnesium sulfate, followed by distilling-off of the solvent to obtain 3.46 g of a crude product.

The crude product was purified by silica gel column chromatography (eluent: hexane/toluene=3/1) to obtain 1.40 g of 2-(4-perfluorooctylphenyl)-5-decyloxypyrimidine (Yield: 30%, m.p.=114° C.).

EXAMPLE 5

A liquid crystal composition A was prepared by mixing the following compounds in the indicated proportions.

| Structural formula | wt. parts |
| --- | --- |
| $C_9H_{19}$—Py2—Ph—$OC_9H_{19}$ | 6 |
| $C_{10}H_{21}$—Py2—Ph—$OC_8H_{17}$ | 6 |
| $C_8H_{17}O$—Pr1—Ph—$O(CH_2)_5$*$CH(CH_3)C_2H_5$ | 7 |
| $C_{11}H_{23}O$—Py2—Ph—$O(CH_2)_2$*$CH(CH_3)C_2H_5$ | 14 |
| $C_{10}H_{21}$—Pr2—Ph—$C_6H_{13}$ | 8 |
| $C_6H_{13}$—Py2—Ph—Ph—$C_4H_9$ | 4 |
| $C_8H_{17}$—Ph—Pr2—Ph—$OC_5H_{11}$ | 2 |
| $C_3H_7$—Cy—COO—Ph—Py1—$C_{12}H_{25}$ | 10 |
| $C_5H_{11}$—Cy—COO—Ph—Py1—$C_{12}H_{25}$ | 5 |
| $C_{10}H_{21}O$—Ph—COS—Ph—$OC_8H_{17}$ | 10 |
| $C_6H_{13}$—Ph—COO—Ph—Ph—$OCH_2CH(CH_3)C_2H_5$ | 7 |
| $C_3H_7$—Cy—$CH_2O$—Ph—Py1—$C_8H_{17}$ | 7 |
| $C_{10}H_{21}$—Ph—Ph—$OCH_2$—$Ph$—$C_7H_{15}$ | 5 |
| $C_{12}H_{25}$—Py2—Ph—$OCH_2$*$CH(F)C_5H_{11}$ | 2 |
| $C_5H_{11}$—Cy—COO—Ph—$OCH_2$*$CH(F)C_6H_{13}$ | 2 |
| $C_{12}H_{25}O$—Ph—Pa—$COO(CH_2)_3$*$CH(CH_3)C_2H_5$ | 2 |
| $C_{12}H_{25}O$—Ph—Pa—$O(CH_2)_3$*$CH(CH_3)OC_3H_7$ | 3 |

The liquid crystal composition A was further mixed with the following example compounds in the indicated proportions to provide a liquid crystal composition B.

| Ex. Comp. No. | Structural formula | wt. parts |
| --- | --- | --- |
| 3 | $C_2H_5O$—Py2—Ph—$C_{17}F_{35}$ | 2 |
| 17 | $C_5H_{11}$—Py2—Ph—$C_{10}F_{21}$ | 1 |
|  | Composition A | 97 |

EXAMPLE 6

Two 0.7 mm-thick glass plates were provided and respectively coated with an ITO film to form an electrode for voltage application, which was further coated with an insulating layer of vapor-deposited $SiO_2$. On the insulating layer, a 0.2%—solution of silane coupling agent (KBM-602, available from Shinetsu Kagaku K.K.) in isopropyl alcohol was applied by spinner coating at a speed of 2000 rpm for 15 second and subjected to hot curing treatment at 120° C. for 20 min.

Further, each glass plate provided with an ITO film and treated in the above described manner was coated with a 1.5%—solution of polyimide resin precursor (SP-510, available from Toray K.K.) in dimethylacetoamide by a spinner coater rotating at 2000 rpm for 15 seconds. Thereafter, the coating film was subjected to heat curing at 300° C. for 60 min. to obtain about 250 Å—thick film. The coating film was rubbed with acetate fiber-planted cloth. The thus treated two glass plates were washed with isopropyl alcohol. After silica beads with an average particle size of 2.0 microns were dispersed on one of the glass plates, the two glass plates were applied to each other with a bonding sealing agent (Lixon Bond, available from Chisso K.K.) so that their rubbed directions were parallel to each other and heated at 100° C. for 60 min. to form a blank cell.

Then, the liquid crystal composition B prepared in Example 5 was heated into an isotropic liquid, and injected into the above prepared cell under vacuum and, after sealing, was gradually cooled to 25° C. at a rate of 20° C./hour to prepare a ferroelectric liquid crystal device. The cell gap was found to be about 2 microns as measured by a Berek compensator.

The ferroelectric liquid crystal device was subjected to measurement of an optical response time (time from voltage application until the transmittance change reaches 90% of the maximum under the application of a peak-to-peak voltage Vpp of 20V in combination with right-angle cross-nicol polarizers) including evaluation of a temperature-dependence of response time (i.e., a ratio of a response time at 10° C. to a response time at 40° C.). The results of the measurement are shown below.

|  | 10° C. | 25° C. | 40° C. |
| --- | --- | --- | --- |
| Response time (μsec) | 570 | 306 | 171 |
| Ratio (10° C./40° C.) | 3.33 |  |  |

Comparative Example 1

A ferroelectric liquid crystal device was prepared and subjected to measurement of response time in the same manner as in Example 6 except for injecting the composition A alone used in Example 5 into a blank cell, whereby the following results were obtained.

|  | 10° C. | 25° C. | 40° C. |
| --- | --- | --- | --- |
| Response time (μsec) | 668 | 340 | 182 |
| Ratio (10° C./40° C.) | 3.67 |  |  |

EXAMPLE 7

A liquid crystal composition C was prepared by mixing the following Example Compounds instead of those of Example 5 in the indicated proportions with the liquid crystal composition A.

| Ex. Comp. No. | Structural formula | wt. parts |
| --- | --- | --- |
| 9 | $C_4H_9$—Py2—Ph—$C_{12}F_{25}$ | 1 |
| 13 | $C_2H_5CH(C_2H_5)CH_2CH_2O$—Py2—Ph—$C_9F_{19}$ | 2 |
|  | Composition A | 94 |

A ferroelectric liquid crystal device was prepared in the same manner as in Example 6 except that the above liquid crystal composition C was used, and the device was subjected to measurement of optical response time and observation of switching states. In the device, a monodomain with a good and uniform alignment characteristic was observed. The results of the measurement are shown below.

|  | 10° C. | 25° C. | 40° C. |
| --- | --- | --- | --- |
| Response time (μsec) | 578 | 312 | 176 |
| Ratio (10° C./40° C.) | 3.28 |  |  |

EXAMPLE 8

A liquid crystal composition D was prepared by mixing the following compounds in the indicated proportions.

| Structural formula | wt. parts |
| --- | --- |
| $C_7H_{15}$—Py2—Ph—$OC_9H_{19}$ | 12 |
| $C_{11}H_{23}$—Py2—Ph—$OC_6H_{13}$ | 10 |
| $C_8H_{17}$—Pr2—Ph—$O(CH_2)_3$*$CH(CH_3)C_2H_5$ | 10 |
| $C_{10}H_{21}$—Py2—Ph—$O(CH_2)_4CH(CH_3)OCH_3$ | 3 |
| $C_8H_{17}$—Py2—Ph—Ph—$OC_6H_{13}$ | 8 |
| $C_6H_{13}O$—Ph—OCO—Np—$OC_9H_{19}$ | 4 |
| $C_3H_7$—Cy—COO—Ph—Py1—$C_{11}H_{23}$ | 6 |
| $C_8H_{17}$—Cy—COO—Ph—Py1—$C_{11}H_{23}$ | 2 |
| $C_5H_{11}$—Cy—COO—Ph—Py1—$C_{11}H_{23}$ | 8 |
| $C_{10}H_{21}O$—Ph—COO—Ph—$OCH_2$*$CH(CH_2)_3C_2H_5$ | 15 |
| $C_4H_9$—Cy—$CH_2O$—Ph—Py1—$C_6H_{13}$ | 7 |
| $C_5H_{11}$—Cy—$CH_2O$—Ph—Py1—$C_6H_{13}$ | 7 |
| $C_9H_{19}O$—Ph—$OCH_2$—Ph—Ph—$C_7H_{15}$ | 4 |
| $C_6H_{13}$*$CH(CH_3)O$—Ph—COO—Ph—Ph—OCO*$CH(CH_3)OC_4H_9$ | 2 |
| $C_{12}H_{25}$—Py2—Ph—OCO*CH(Cl)*$CH(CH_3)C_2H_5$ | 2 |

The liquid crystal composition D was further mixed with the following compounds in the proportions indicated below to provide a liquid crystal composition E.

| Ex. Comp. No. | Structural Formula | wt. parts |
| --- | --- | --- |
| 27 | $C_7H_{15}$—Py2—Ph—$C_7F_{15}$ | 2 |
| 34 | $C_9H_{19}$—Py2—Ph—$C_6F_{13}$ | 2 |
| | Composition D | 96 |

A ferroelectric liquid crystal device was prepared in the same manner as in Example 6 except that the above liquid crystal composition E was used, and the device was subjected to measurement of optical response time and observation of switching states. In the device, a monodomain with a good and uniform alignment characteristic was observed. The results of the measurement are shown below.

| | 10° C. | 25° C. | 40° C. |
| --- | --- | --- | --- |
| Response time (μsec) | 623 | 321 | 175 |
| Ratio (10° C./40° C.) | 3.56 | | |

Comparative Example 2

A ferroelectric liquid crystal device was prepared and subjected to measurement of response time in the same manner as in Example 6 except for injecting the composition D alone used in Example 8 into a blank cell, whereby the following results were obtained.

| | 10° C. | 25° C. | 40° C. |
| --- | --- | --- | --- |
| Response time (μsec) | 784 | 373 | 197 |
| Ratio (10° C./40° C.) | 3.98 | | |

EXAMPLE 9

A liquid crystal composition F was prepared by mixing the following Example Compounds instead of those of Example 8 in the indicated proportions with the liquid crystal composition D.

| Ex. Comp. No. | Structural formula | wt. parts |
| --- | --- | --- |
| 4 | $C_2H_5$—Py2—Ph—$C_{10}F_{21}$ | 2 |

-continued

| Ex. Comp. No. | Structural formula | wt. parts |
| --- | --- | --- |
| 25 | $C_2H_5CH(CH_3)(CH_2)_5$—Py2—Ph—$C_{10}F_{21}$ | 2 |
| | Composition D | 96 |

A ferroelectric liquid crystal device was prepared in the same manner as in Example 6 except that the above liquid crystal composition F was used, and the device was subjected to measurement of optical response time and observation of switching states. In the device, a monodomain with a good and uniform alignment characteristic was observed. The results of the measurement are shown below.

| | 10° C. | 25° C. | 40° C. |
| --- | --- | --- | --- |
| Response time (μsec) | 629 | 325 | 178 |
| Ratio (10° C./40° C.) | 3.53 | | |

As apparent from the above Examples 5 to 9, the ferroelectric liquid crystal device including the liquid crystal compositions B, C, E and F i.e., compositions containing an optically inactive mesomorphic compound of the formula (I) according to the present invention, provided improved operation characteristic at a lower temperature, high speed responsiveness and a decreased temperature-dependence of response speed.

EXAMPLE 10

A blank cell was prepared in the same manner as in Example 6 by using a 2% aqueous solution of polyvinyl alcohol resin (PVA-117, available from Kuraray K.K.) instead of the 1.5%-solution of polyimide resin precursor in dimethylacetoamide on each electrode plate. A ferroelectric liquid crystal device was prepared by filling the blank cell with the liquid crystal composition B used in Example 5. The liquid crystal device was subjected to measurement response time in the same manner as in Example 6. The results are shown below.

| | 10° C. | 25° C. | 40° C. |
| --- | --- | --- | --- |
| Response time (μsec) | 565 | 304 | 169 |
| Ratio (10° C./40° C.) | 3.34 | | |

EXAMPLE 11

A blank cell was prepared in the same manner as in Example 6 except for omitting the $SiO_2$ layer to form an alignment control layer composed of the polyimide resin layer alone on each electrode plate. A ferroelectric liquid crystal device was prepared by filling such a blank cell with liquid crystal composition B used in Example 5. The liquid crystal device was subjected to measurement of response time in the same manner as in Example 6. The results are shown below.

|  | 10° C. | 25° C. | 40° C. |
|---|---|---|---|
| Response time (μsec) | 558 | 298 | 165 |
| Ratio (10° C./40° C.) | 3.38 | | |

As is apparent from the above Examples 10 and 11, also in the case of a different device structure, the device containing the ferroelectric liquid crystal composition B according to the present invention provided an improved low-temperature operation characteristic and a decreased temperature dependence of response speed similarly as in Example 6.

EXAMPLE 12

A liquid crystal composition G was prepared by mixing the following compounds in the indicated proportions.

| Structural formula | wt. parts |
|---|---|
| $C_6H_{13}$—Py2—Ph—$O(CH_2)_4C_3F_7$ | 5 |
| $C_{11}H_{23}$—Py2—Ph—$OCH_2C_4F_9$ | 10 |
| $C_8H_{17}O$—Pr1—Ph—$O(CH_2)_5CH(CH_3)C_2H_5$ | 5 |
| $C_{10}H_{21}$—Py2—Ph—$O(CH_2)_4CH(CH_3)OCH_3$ | 10 |
| $C_6H_{13}$—Py2—Ph—Ph—$C_8H_{17}$ | 7 |
| $C_8H_{17}$—Py2—Ph—$OC_6H_{13}$ | 15 |
| $C_5H_{11}$—Cy—COO—Ph—Py1—$C_{12}H_{25}$ | 5 |
| $C_4H_9$—Cy—COO—Ph—Py1—$C_{11}H_{23}$ | 5 |
| $C_3H_7$—Cy—COO—Ph—Py1—$C_{11}H_{23}$ | 5 |
| $C_{12}H_{25}O$—Ph—Pa—$CO(CH_2)_3$*$CH(CH_3)C_2H_5$ | 2 |
| $C_{10}H_{21}$—Py2—Ph—$OCH_2$*$CH(F)C_2H_5$ | 5 |
| $C_6H_{13}$—Cy—COO—Ph—$OCH_2$*$CH(F)C_6H_{13}$ | 2 |
| $C_8H_{17}$—Ph—OCO—Ph—Ph—$CH(CH_3)OCOC_6H_{13}$ | 6 |
| $C_8H_{17}$—Py2—Ph—OCO—Ph—F | 3 |
| $C_6H_{13}O$—Btb2—Ph—$OCO(CH_2)_6C_2F_5$ | 3 |
| $C_8H_{17}O$—Ph—COS—Ph—$OCH_2C_3F_7$ | 10 |

The liquid crystal composition G was further mixed with the following example compounds in the indicated proportions to provide a liquid crystal composition H.

| Ex. Comp. No. | Structural formula | wt. parts |
|---|---|---|
| 10 | $C_4H_9O$—Py2—Ph—$C_9F_{19}$ | 3 |
| 31 | $C_8H_{17}$—Py2—Ph—$C_{10}F_{21}$ | 3 |
|  | Composition G | 94 |

Two 0.7 mm-thick glass plates were provided and respectively coated with an ITO film to form an electrode for voltage application, which was further coated with an insulating layer of vapor-deposited $SiO_2$. On the insulating layer, a 0.2%-solution of silane coupling agent (KBM-602, available from Shinetsu Kagaku K.K.) in isopropyl alcohol was applied by spinner coating at a speed of 2000 rpm for 15 second and subjected to hot curing treatment at 120° C. for 20 min.

Further, each glass plate provided with an ITO film and treated in the above described manner was coated with a 1.0%-solution of polyimide resin precursor (SP-510, available from Toray K.K.) in dimethylacetoamide by a spinner coater rotating at 3000 rpm for 15 seconds. Thereafter, the coating film was subjected to heat curing at 300° C. for 60 min. to obtain about 120 Å-thick film. The coating film was rubbed with acetate fiber-planted cloth. The thus treated two glass plates were washed with isopropyl alcohol. After silica beads with an average particle size of 1.5 microns were dispersed on one of the glass plates, the two glass plates were applied to each other with a bonding sealing agent (Lixon Bond, available from Chisso K.K.) so that their rubbed directions were parallel to each other and heated at 100° C. for 60 min. to form a blank cell. The cell gap was found to be about 1.5 microns as measured by a Berek compensator.

Then, the liquid crystal composition H prepared above was heated into an isotropic liquid, and injected into the above prepared cell under vacuum and, after sealing, was gradually cooled to 25° C. at a rate of 20° C./hour to prepare a ferroelectric liquid crystal device.

The ferroelectric liquid crystal device was subjected to measurement of a contrast ratio at 30° C. when the device was driven by applying a driving voltage waveform shown in FIGS. 5A and 5B (bias ratio=⅓), whereby a contrast ratio at 30° C. of 21.0 was obtained.

Comparative Example 3

A ferroelectric liquid crystal device was prepared and subjected to measurement of a contrast ratio in the same manner as in Example 12 except for injecting the composition G alone used in Example 12 into a blank cell, whereby a contrast ratio of 8.1 was obtained.

EXAMPLE 13

A liquid crystal composition I was prepared by mixing the following Example Compounds instead of those of Example 12 in the indicated proportions with the liquid crystal composition G.

| Ex. Comp. No. | Structural formula | wt. parts |
|---|---|---|
| 23 | $C_7H_{15}O$—Py2—Ph—$C_6F_{13}$ | 3 |
| 48 | $C_8H_{17}$—Py2—Ph—$C_8F_{17}$ | 3 |
|  | Composition G | 94 |

A ferroelectric liquid crystal device was prepared in the same manner as in Example 12 except that the above liquid crystal composition I was used, and the device was subjected to measurement of a contrast ratio, whereby a contrast ratio of 23.1 was obtained.

EXAMPLE 14

A liquid crystal composition J was prepared by mixing the following Example Compounds instead of those of Example 12 in the indicated proportions with the liquid crystal composition G.

| Ex. Comp. No. | Structural formula | wt. parts |
|---|---|---|
| 2 | $C_{14}H_{29}$—Py2—Ph—$C_3F_7$ | 2 |
| 33 | $C_8H_{17}O$—Py2—Ph—$C_{12}F_{25}$ | 2 |
| 50 | $C_{10}H_{21}$—Py2—Ph—$C_5F_{11}$ | 2 |
|  | Composition G | 94 |

A ferroelectric liquid crystal device was prepared in the same manner as in Example 12 except that the above liquid crystal composition J was used, and the device was subjected to measurement of a contrast ratio, whereby a contrast ratio of 20.9 was obtained.

EXAMPLE 15

A liquid crystal composition K was prepared by mixing the following Example Compounds instead of those of Example 12 in the indicated proportions with the liquid crystal composition G.

| Ex. Comp. No. | Structural formula | wt. parts |
|---|---|---|
| 16 | $C_5H_{11}$—Py2—Ph—$C_5F_{11}$ | 3 |
| 40 | $C_{10}H_{21}$—Py2—Ph—$C_6F_{13}$ | 5 |
|  | Composition G | 92 |

A ferroelectric liquid crystal device was prepared in the same manner as in Example 12 except that the above liquid crystal composition K was used, and the device was subjected to measurement of a contrast ratio, whereby a contrast ratio of 20.8 was obtained.

As apparent from the above Examples 12 to 15, the ferroelectric liquid crystal device including the liquid crystal compositions H, I, J and K, i.e., compositions containing an optically inactive mesomorphic compound of the formula (I) according to the present invention, provided improved a higher contrast ratio when driven.

EXAMPLE 16

A blank cell was prepared in the same manner as in Example 12 by using a 2% aqueous solution of polyvinyl alcohol resin (PVA-117, available from Kuraray K.K.) instead of the 1.0%-solution of polyimide resin precursor in dimethylacetoamide on each electrode plate. A ferroelectric liquid crystal device was prepared by filling the blank cell with the liquid crystal composition H used in Example 12. The liquid crystal device was subjected to measurement a contrast ratio in the same manner as in Example 12, whereby a contrast ratio of 23.0 was obtained.

EXAMPLE 17

A blank cell was prepared in the same manner as in Example 12 except for omitting the $SiO_2$ layer to form an alignment control layer composed of the polyimide resin layer alone on each electrode plate. A ferroelectric liquid crystal device was prepared by filling such a blank cell with liquid crystal composition H used in Example 12. The liquid crystal device was subjected to measurement of a contrast ratio in the same manner as in Example 12, whereby a contrast ratio of 17.0 was obtained.

EXAMPLE 18

A blank cell was prepared in the same manner as in Example 12 except that a 1.0%-solution of polyamide acid (LQ-1802, available from Hitachi Kasei K.K.) in NMP (N-methylpyrrolidone) was formed instead of the 1.0%-solution of polyimide resin precursor in dimethylacetoamide on each electrode plate and that the hot curing treatment thereof was effected at 270° C. for 1 hour. A ferroelectric liquid crystal device was prepared by filling the blank cell with the liquid crystal composition K used in Example 15. The liquid crystal device was subjected to measurement a contrast ratio in the same manner as in Example 15, whereby a contrast ratio of 25.2 was obtained.

As is apparent from the above Examples 16, 17 and 18, also in the case of a different device structure, the device containing the ferroelectric liquid crystal composition H or K according to the present invention provided a higher contrast ratio similarly as in Example 15.

Further, when a driving voltage waveform different from that used in Example 15 was used, liquid crystal devices using the liquid crystal composition H or K respectively prepared in the same manner as in Examples 16–18 according to the present invention provided a higher contrast ratio compared with liquid crystal devices using a liquid crystal composition G containing no mesomorphic compound of the formula (I) of the present invention.

As described hereinabove, according to the present invention, by utilizing a ferroelectricity exhibited by a liquid crystal composition containing at least one mesomorphic compound of the formula (I), there is provided a liquid crystal device providing improved characteristic such as a good alignment characteristic, a good switching property, high-speed responsiveness, a decreased temperature-dependence of response speed, a high contrast ratio, and a stable layer structure of liquid crystal molecules.

In addition, when the liquid crystal device is used as a display device in combination with a light source, drive circuit, etc., a liquid crystal apparatus, such as a liquid crystal display apparatus, providing good display characteristics can be realized.

What is claimed is:

1. An optically inactive mesomorphic compound represented by the following formula (I):

$$R-\underset{N}{\underset{\|}{\bigcirc}}-\bigcirc-C_mF_{2m+1},\qquad(I)$$

wherein R denotes a linear or branches alkyl group having 1–18 carbon atoms or a linear or branched alkoxy group having 1–18 carbon atoms; and m is an integer of 6–18.

2. A compound according to claim 1, wherein R denotes a linear alkyl group having 3–14 carbon atoms or a linear alkoxy group having 3–14 carbon atoms.

3. A compound according to claim 1, wherein m is an integer of 9–18.

4. A liquid crystal composition comprising at least two different compounds, at least one of which is an optically inactive mesomorphic compound of the formula (I) according to any one of claim 1, 2 or 3.

5. A liquid crystal composition comprising at least three different compounds, at least two of which are optically inactive mesomorphic compounds of the formula (I) according to any one of claim 1, 2 or 3.

6. A liquid crystal composition according to claim 4, which comprises 1–80 wt. % of an optically inactive mesomorphic compound of the formula (I).

7. A liquid crystal composition according to claim 4, which comprises 1–60 wt. % of an optically inactive mesomorphic compound of the formula (I).

8. A liquid crystal composition according to claim 4, which comprises 1–40 wt. % of an optically inactive mesomorphic compound of the formula (I).

9. A liquid crystal composition according to claim 4, which has a chiral smectic phase.

10. A liquid crystal device, including a liquid crystal composition according to claim 4.

11. A liquid crystal device, comprising a pair of substrates and a liquid crystal composition according to claim 4 disposed between the substrates.

12. A device according to claim 11, which further comprises an alignment control layer.

13. A device according to claim 12, wherein the alignment control layer has been subjected to uniaxial alignment treatment.

14. A device according to claim 11, wherein the liquid crystal composition is disposed in a thickness suppressing formation of a helical structure of liquid crystal molecules between the substrates.

15. A liquid crystal apparatus comprising a liquid crystal device according to claim 10.

16. An apparatus according to claim 15, wherein the liquid crystal device is used as a display device.

17. An apparatus according to claim 15, which further comprises a drive circuit for the liquid crystal device.

18. An apparatus according to claim 16, which further comprises a light source.

19. A display method, comprising:

providing a liquid crystal composition according to claim 4; and controlling the alignment direction of liquid crystal molecules to effect display.

* * * * *

UNITED STATES PATENT AND TRADEMARK OFFICE
CERTIFICATE OF CORRECTION

PATENT NO. : 5,593,616

DATED : January 14, 1997

INVENTOR(S): SHINICHI NAKAMURA ET AL.

It is certified that error appears in the above-identified patent and that said Letters Patent is hereby corrected as shown below:

Title page, item
[54] TITLE, and col. 1,

Line 1, "INACTIVE," should read --INACTIVE--.

Item
[56] REFERENCES CITED

Foreign Patent Documents, "1233262 9/1989 Japan" should read "1-233262 9/1989 Japan.--.
    Foreign Patent Documents, "1230548 9/1989 Japan" should read --1-230548 9/1989 Japan.--.
    Foreign Patent Documents, "2069443 3/1990 Japan." should read --2-069443 3/1990 Japan.--.
    Foreign Patent Documents, "2142753 5/1990 Japan." should read --2-142753 5/1990 Japan.--.
    Foreign Patent Documents, "3093748 4/1991 Japan." should read --3-093748 4/1991 Japan.--.
    Foreign Patent Documents, "26679 1/1992 Japan" should be deleted.
    Foreign Patent Documents, "4026679 1/1992 Japan" should read --4-026679 1/1992 Japan--.

Item
[57] ABSTRACT

Line 5, "2-18," should read --6-18,--.

COLUMN 1

Line 1, "INACTIVE," should read --INACTIVE--.

UNITED STATES PATENT AND TRADEMARK OFFICE
CERTIFICATE OF CORRECTION

PATENT NO. : 5,593,616

DATED : January 14, 1997

INVENTOR(S) : SHINICHI NAKAMURA ET AL.

It is certified that error appears in the above-identified patent and that said Letters Patent is hereby corrected as shown below:

COLUMN 2

Line 29, "electric" should read --electric field--.

COLUMN 3

Line 39, "tile" should read --tilt--.

COLUMN 4

Line 27, "2-18." should read --6-18.--.
Line 58, "$(C_MF_{2M-1})$" should read --$(C_MF_{2M+1})$.

COLUMN 5

Line 43, "DESCRIPTION" should read --BRIEF DESCRIPTION--.
Line 52, "$\hat{H}$" should read --Ⓗ--.

COLUMN 6

Line 57, "(50)" should read --(50))--.

COLUMN 7

Line 9, "$C_4H_9$-" should read --$C_4H_9O$- --.
Line 60, "-Ph'$C_9F_{19}$" should read -- -Ph-$C_9F_{19}$--.

COLUMN 13

Line 38, "C" should be italic and "D" should be ital...

UNITED STATES PATENT AND TRADEMARK OFFICE
CERTIFICATE OF CORRECTION

PATENT NO.  : 5,593,616
DATED       : January 14, 1997
INVENTOR(S) : SHINICHI NAKAMURA ET AL.

It is certified that error appears in the above-identified patent and that said Letters Patent is hereby corrected as shown below:

COLUMN 20

Line 2, "$-(CH_2)_c-$" should read -- $-(CH_2)_c-$ --.
Line 7, "C" should be italic and "D" should be italic.

COLUMN 21

Line 15, "bond" should read --bond,--.

COLUMN 25

Line 30, "one" should read --one of--.

COLUMN 26

Line 9, "$-(CH_2)_c-$" should read -- $-(CH_2)_c-$ --.
Line 13, "C" should be italic and "D" should be italic.

COLUMN 27

Line 35, "$-(CH_2)_c-$" should read -- $-(CH_2)_c-$ --.
Line 39, "C" should be italic and "D" should be italic.
Line 44, "(XVIII);" should read --(XVIII),--.

COLUMN 28

Line 1, "and" should be deleted.
Line 3, "The compounds of the formula (XVIa) and" should be deleted.
Line 10, "formula" should read --formulae--.

UNITED STATES PATENT AND TRADEMARK OFFICE
CERTIFICATE OF CORRECTION

PATENT NO. : 5,593,616

DATED : January 14, 1997

INVENTOR(S) : SHINICHI NAKAMURA ET AL.

It is certified that error appears in the above-identified patent and that said Letters Patent is hereby corrected as shown below:

COLUMN 28

Line 12, "(XVIa) to (XVIc):" should read --(XVIaa to (XVIbc):--.

COLUMN 31

Line 55, "in" (second occurrence) should read --was added, and the mixture heated--.

COLUMN 32

Line 5, "2.0 9" should read --2.0 g--.
Line 9, "in" (second occurrence) should read --was added, and the mixture heated--.

COLUMN 32

Line 16, "silica" should read --silica gel--.
Line 30, "in" (second occurrence) should read --was added, and the mixture heated--.
Line 60, "in" (second occurrence) should read --was added, and the mixture heated--.

COLUMN 33

Line 22, "-OCH$_2$-Ph-C$_7$H$_{15}$" should read -- -OCH$_2$-Ph-C$_7$H$_{15}$--.
Line 45, "0.2%—solution" should read --0.2%-solution--.
Line 48, "second" should read --seconds--.
Line 52, "1.5%—solution" should read --1.5%-solution--.
Line 56, "Å—thick" should read --Å-thick--.

UNITED STATES PATENT AND TRADEMARK OFFICE
CERTIFICATE OF CORRECTION

PATENT NO. : 5,593,616

DATED : January 14, 1997

INVENTOR(S): SHINICHI NAKAMURA ET AL.

It is certified that error appears in the above-identified patent and that said Letters Patent is hereby corrected as shown below:

COLUMN 35

Line 11, "*CH(CH$_2$)$_3$C$_2$H$_5$" should read --*CH(CH$_3$)C$_2$H$_5$--.

COLUMN 36

Line 40, "F" should read --F,--.

COLUMN 37

Line 39, "3" should read --2--.
  After line 39, insert --C$_7$H$_{15}$O-Ph-Tz1-Ph-C$_5$H$_{11}$    3--.
  Line 60, "second" should read --seconds--.

COLUMN 39

Line 26, "a" should read --(a--.
  Line 27, "higher" should read --higher)--.
  Line 38, "a" should read --of a--.
  Line 65, "a" should read --of a--.

UNITED STATES PATENT AND TRADEMARK OFFICE
CERTIFICATE OF CORRECTION

PATENT NO. : 5,593,616

DATED : January 14, 1997

INVENTOR(S): SHINICHI NAKAMURA ET AL.

Page 6 of 6

It is certified that error appears in the above-identified patent and that said Letters Patent is hereby corrected as shown below:

<u>COLUMN 40</u>

Line 36, "branches" should read --branched--.
Line 47, "claim" should read --claims--.
Line 51, "claim" should read --claims--.

Signed and Sealed this

Twenty-ninth Day of July, 1997

Attest:

BRUCE LEHMAN

*Attesting Officer*     *Commissioner of Patents and Trademarks*